United States Patent [19]

Gammill et al.

[11] Patent Number: 5,132,400
[45] Date of Patent: Jul. 21, 1992

[54] PEPTIDES CONTAINING A (1-AMINO-2-HYDROXY-2-HETEROCYCLIC-)ETHYL MOIETY

[75] Inventors: Ronald B. Gammill, Kalamazoo; Tomi K. Sawyer, Portage, both of Mich.

[73] Assignee: The Upjohn Company, Kalamazoo, Mich.

[21] Appl. No.: 511,273

[22] Filed: Apr. 20, 1990

Related U.S. Application Data

[63] Continuation-in-part of PCT/US88/03274, Sep. 26, 1988, which is a continuation-in-part of Ser. No. 11,847, Oct. 21, 1987, abandoned.

[51] Int. Cl.$^5$ ............................ C07K 5/12; C07K 5/06
[52] U.S. Cl. .................................... 530/317; 530/330; 530/331
[58] Field of Search .................... 530/331, 330, 317

[56] References Cited

U.S. PATENT DOCUMENTS

| | | | |
|---|---|---|---|
| 4,713,445 | 12/1987 | Szelke et al. | 530/330 |
| 4,880,781 | 11/1989 | Hester, Jr. et al. | 514/18 |
| 4,885,292 | 12/1989 | Ryono et al. | 514/211 |

FOREIGN PATENT DOCUMENTS

| | | |
|---|---|---|
| 0173481 | 5/1985 | European Pat. Off. |
| 0231919 | 2/1987 | European Pat. Off. |

OTHER PUBLICATIONS

Burger, *Medicinal Chemistry*, 1960, pp. 565–571, 578–581, 600–601.
Denkwalter et al., *Progress In Drug Research*, 1966, vol. 10, pp. 610–612.
Plattner et al., *J. Med. Chem.* 1988, vol. 31(12):2277–2288.
Bolis et al., *J. Med. Chem.*, 1987, vol. 30(10):1729–1737.
Haber et al., *J. Cardiovasc. Pharmacol.* 1987, vol. 10(Supp. 7):554–558.
D. E. Ryono et al., Potent Inhibitors of Hog and Human Renin Containing an Amino Alcohol Dipeptide Surrogate, Proc. of the 9th Amer. Peptide Symposium, Toronto, Canada, 739–42 (1985).
J. G. Dann et al., Human Renin: A New Class of Inhibitors, Biochemical and Biophysical Research Communications 134 (No. 1): 71–77 (1986).
D. H. Rich, Inhibitors of Aspartic Proteinases, Proteinase Inhibitors, Chapter 5, Elsevier Science Publishers BV (1986).

*Primary Examiner*—Merrell C. Cashion, Jr.
*Assistant Examiner*—Choon P. Koh
*Attorney, Agent, or Firm*—Martha A. Gammill

[57] ABSTRACT

The present invention provides novel peptides of the formula $X-A_6-B_7-C_8-D_9-E_{10}-F_{11}$ containing a novel (1-amino-2-hydroxy-2-heterocyclic) ethyl moiety of the formula $XL_{2c}$ at the $E_{10}-F_{11}$-position, X is a terminal group, and the remaining variables are amino acid residues. The present invention also provides novel intermediate compounds. These peptides are useful as renin inhibitors and as inhibitors of retroviral proteases. Renin inhibitors are useful for the diagnosis and control of renin-dependent hyperaldosterism, other renin-dependent cardiovascular disorders and ocular disorders. Inhibitors of retroviral proteases, such as the HIV-I protease, are useful for treating diseases caused by retroviruses, such as human acquired immunodificiency disease syndrome (AIDS).

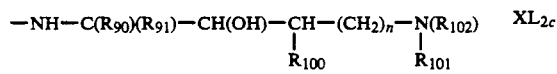

4 Claims, No Drawings

PEPTIDES CONTAINING A (1-AMINO-2-HYDROXY-2-HETEROCYCLIC-)ETHYL MOIETY

CROSS REFERENCE TO RELATED APPLICATIONS

The present application is a continuation-in-part application of PCT application, Ser. No. PCT/US 07/03274, filed Sep. 26, 1988 now pending, which is a continuation-in-part of U.S. patent application Ser. No. 07/111,847, filed Oct. 21, 1987, now abandoned.

BACKGROUND OF THE INVENTION

The present invention provides novel compounds. More particularly, the present invention provides novel peptide analogs and intermediates thereto. Most particularly, the present invention provides compounds having a (1-cyclohexylmethyl-1-amino-2-hydroxy-2-(2-pyrrolidinyl))ethyl end function. The peptides provided herein are useful as renin inhibitors and as inhibitors of retroviral proteases. Renin inhibitors are useful for the diagnosis and control of renin-dependent hypertension, congestive heart failure, renin-dependent hyperaldosterism, and other renin-dependent cardiovascular disorders. Inhibitors of retroviral proteases, such as the HIV-I protease, are useful for treating diseases caused by retroviruses, such as human acquired immunodeficiency disease syndrome (AIDS).

Renin is an endopeptidase which specifically cleaves a particular peptide bond of its substrate (angiotensinogen), of which the N-terminal sequence in equine substrate is for example:

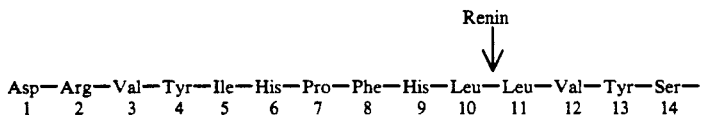

IA as found by L. T. Skeggs et al. J. Exper. Med. 106, 439 (1957). Human renin substrate has a different sequence as recently discovered by D. A. Tewkesbury et al, Biochem. Biophys. Res. Comm. 99, 1311 (1981). It may be represented as follows:

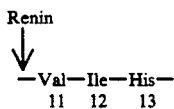

IB and having the sequence to the left of the arrow (↓) being as designated in formula IA above.

Renin cleaves angiotensinogen to produce angiotensin I, which is converted to the potent pressor angiotensin II. A number of angiotensin I converting enzyme inhibitors are known to be useful in the treatment of hypertension. Inhibitors of renin may also be useful in the treatment of hypertension.

A number of renin-inhibitory peptides have been disclosed. Thus, U.S. Pat. No. 4,424,207; European published applications 45,665; 104,041; and 156,322; and U.S. patent application Ser. No. 825,250, filed Feb. 3, 1986; disclose certain peptides with the dipeptide at the 10,11-position containing an isostere bond. A number of statine derivatives stated to be renin inhibitors have been disclosed, see, e.g., European published applications 77,028; 81,783; 114,993; 156,319; and 156,321; and U.S. Pat. Nos. 4,478,826; 4,470,971; 4,479,941; and 4,485,099. Terminal disulfide cycles have also been disclosed in renin inhibiting peptides; see, e.g., U.S. Pat. Nos. 4,477,440 and 4,477,441. Aromatic and aliphatic amino acid residues at the 10,11 position of the renin substrate are disclosed in U.S. Pat. Nos. 4,478,827 and 4,455,303. Renin inhibitors containing a C-terminal amide cycle are disclosed in U.S. Pat. No. 4,485,099 and European published applications 156,320 and 156,318. Certain tetrapeptides are disclosed in European publications 111,266 and 77,027. Further, European published application No. 118,223 discloses certain renin inhibiting peptide analogs where the 10–11 peptide link is replaced by a one to four atom carbon or carbon-nitrogen link. Additionally, Holladay et al., in "Synthesis of Hydroxyethylene and Ketomethylene Dipeptide Isosteres", Tetrahedron Letters, Vol. 24. No. 41, pp. 4401–4404, 1983 disclose various intermediates in a process to prepare stereo-directed "ketomethylene" and "hydroxyethylene" dipeptide isosteric functional groups disclosed in the above noted U.S. Pat. No. 4,424,207. Evans, et al., J. Org. Chem., 50, 4615 (1985) discloses the synthesis of Hydroxyethylene Dipeptide Isosteres. See also, published European patent application 163,237, which discloses certain renin inhibitoring peptides.

Additionally, published European Applications 45,161 and 53,017 disclose amide derivatives useful as inhibitors of angiotensin converting enzymes.

Certain dipeptide and tripeptides are disclosed in U.S. Pat. Nos. 4,514,332; 4,510,085; and 4,548,926 as well as in European published applications 128,762; 152,255; and 181,110. Pepstatin derived renin inhibitors have been disclosed in U.S. Pat. No. 4,481,192. Retroinverso bond modifications at positions 10–11 have been disclosed in U.S. Pat. No. 4,560,505 and in European published applications 127,234 and 127,235. Derivatives of isosteric bond replacements at positions 10–11 have been disclosed in European published applications 143,746 and 144,290; and U.S. patent application Ser. No. 904,149, filed Sep. 5, 1986. Isosteric bond modifications at positions 11–12 and 12–13 have been disclosed in European published application 179,352. Certain peptides containing 2-substituted statine analogues have been disclosed in European published application 157,409. Certain peptides containing 3-aminodeoxystatine have been disclosed in European published application 161,588. Certain peptides containing 1-amino-2-hydroxybutane derivatives at positions 10–11 have been disclosed in European published application 172,346. Certain peptides containing 1-amino-2-hydroxypropane derivatives at positions 10–11 have been disclosed in European published application 172,347. Certain peptides containing N-terminal amide cycles have been disclosed in U.S. patent application Ser. No. 844,716, filed Mar. 27, 1986. Certain peptides containing dihalostatine have been disclosed in PCT application, Ser. No. 000,713, filed Apr. 7, 1986. Certain peptides containing C-terminus truncated epoxy or azido or cyano groups or containing a position 10-11 diol and a position 11-12 retro bond have been disclosed in U.S. patent application Ser. No. 945,340, filed Dec. 22, 1986.

European published applications 156,322; 114,993; and 118,223; and PCT patent application, Ser. No. 002,227, filed Nov. 21, 1986; U.S. patent application Ser. No. 825,250, filed Feb. 3, 1986; U.S. patent application Ser. No. 904,149, filed Sep. 5, 1986; and U.S. patent application Ser. No. 844,716, filed Mar. 27, 1986; disclose hydroxamic acids or esters at the C-terminus.

E.P. 189,203 discloses new N-dihydroxyalkyl peptide derivatives which are useful as inhibitors of renin for treating hypertension.

E.P. 184,855 discloses new hydroxy substituted-statine peptide derivatives which are useful as inhibitors of renin for treating hypertension.

Derivatives of isosteric bond replacements at positions 10-11 as dihydroxy ethylene isosteres have been disclosed in U.S. patent application Ser. No. 904,149, filed Sep. 5, 1986.

A review of the theoretical principles of such transition-state mimetics of renin inhibitors have been recently reviewed in D. H. Rich, Chapter 5, "Inhibitors of Aspartic Proteinases," Proteinase Inhibitors, Elsevier Science Publishers BV (Biochemical Division) (1986).

The following references disclose additional substituents at the 10, 11-position: A. Spaltenstein, P. Carpino, F. Miyake and P. B. Hyskins, Tetrahedron Letters, 27:2095 (1986); D. H. Rich and M. S. Bernatowicz, J. Med. Chem., 25:791 (1982); Roger, J. Med. Chem., 28:1062 (1985); D. M. Glick et al., Biochemistry, 21:3746 (1982); D. H. Rich, Biochemistry, 24:3165 (1985); R. L. Johnson, J. Med. Chem., 25:605 (1982); R. L. Johnson and K. Verschovor, J. Med. Chem., 26:1457 (1983); R. L. Johnson, J. Med. Chem., 27:1351 (1984); P. A. Bartlett and W. B. Kezer et al., J. Am. Chem. Soc., 106:4282 (1984); Peptides: Synthesis, Structure and Function (V. J. Hruby; D. H. Rich, eds.) Proc. 8th American Peptide Sym., Pierce Chemical Company, Rockford, Ill., pp. 511-20; 587-590 (1983).

The preparation of cyclopropyl-containing renin inhibiting peptides is disclosed in U.S. patent application Ser. No. 023,404, filed Mar. 9, 1987, which is incorporated by reference herein.

INFORMATION DISCLOSURE

Structure-activity data have been reported on aminoalcohol isosteres of the $P_1-P_1$, dipeptide which contain an additional carbon atom in the $P_1-P_1$, linkage for stabilization of the aminal function. D. E. Ryono et al., "Potent Inhibitors of Hog and Human Renin Containing an Amino Alcohol Dipeptide Surrogate," Peptides: Structure and Function (Proceedings of the 9th Amer. Peptide Symposium, Toronto, Canada, 739-42 (1985) (Squibb); J. G. Dann et al., "Human Renin: A New Class of Inhibitors," Biochemical and Biophysical Research Communications 134:71-77 (1986) (Wellcome).

A review of the theoretical principles of transition-state mimetics of renin inhibitors have been recently reviewed in D. H. Rich, Chapter 5, "Inhibitors of Aspartic Proteinases," Proteinase Inhibitors, Elsevier Science Publishers BV (Biomedical Division) (1986).

SUMMARY OF THE INVENTION

The present invention particularly provides:
A peptide of the formula I
wherein X is
 (a) hydrogen,
 (b) $C_1-C_7$alkyl,
 (c) $-(CH_2)_p$-aryl,
 (d) $-(CH_2)_p$-Het,
 (e) $-(CH_2)_p-C_3-C_3-C_7$cycloalkyl,
 (f) $R_5-O-CH_2-C(O)-$,
 (g) $R_5-CH_2-O-C(O)-$,
 (h) $R_5-O-C(O)-$,
 (i) $R_5-(CH_2)_n-C(O)-$,
 (j) $R_5-(CH_2)_n-C(S)-$,
 (k) $R_4N(R_4)-(CH_2)_n-C(O)-$,
 (l) $R_5-SO_2-(CH_2)_q-C(O)-$,
 (m) $R_5-SO_2-(CH_2)_q-O-C(O)-$ or
 (n) $R_6-(CH_2)_r-C(O)-$;

wherein $A_6$ is a divalent moiety of the formula $XL_2$;
wherein $B_7$ is a divalent moiety of the formula $XL_b$;
wherein $C_8$ is a divalent moiety of the formula $XL_2$
wherein $D_9$ is a divalent moiety of the formula $XL_3$;
wherein $E_{10}-F_{11}$ is a moiety of the formula $XL_{2c}$;
wherein $R_4$ at each occurrence is the same or different and is
 (a) hydrogen,
 (b) $C_1-C_7$alkyl,
 (c) $-(CH_2)_p$-aryl,
 (d) $-(CH_2)_p$-Het,
 (e) $-(CH_2)_p-C_3-C_3-C_7$cycloalkyl, or
 (f) 1- or 2-adamantyl;
wherein $R_5$ is
 (a) $C_1-C_2$alkyl,
 (b) $C_3-C_7$cycloalkyl,
 (c) aryl,
 (d) -Het, or
 (e) 5-oxo-2-pyrrolidinyl;
wherein $R_6$ is
 (a) hydrogen,
 (b) $C_1-C_7$alkyl,
 (c) $-(CH_2)_p$-aryl,
 (d) $-(CH_2)_p$-Het,
 (e) $-(CH_2)_p-C_3-C_3-C_7$cycloalkyl, or
 (f) 1- or 2-adamantyl;
wherein $R_7$ is
 (a) hydrogen,
 (b) $C_1-C_5$alkyl,
 (c) hydroxy,
 (d) amino $C_1-C_4$alkyl-,
 (e) guanidinyl $C_1-C_3$alkyl-,
 (f) aryl,
 (g) -Het,
 (h) methylthio,
 (i) $-(CH_2)p-C_3-C_7$cycloalkyl, or
 (j) amino;
wherein $R_{26}$ is
 (a) hydrogen,
 (b) $C_1-C_3$alkyl-,
 (c) phenyl-$C_1-C_3$alkyl-;
wherein $R_{90}$ and $R_{91}$ are the same or different and are;
 (a) hydrogen,
 (b) $C_1-C_7$alkyl,
 (c) $-(CH_2)_p$-aryl,
 (d) $-(CH_2)_p$-Het,
 (e) $-(CH_2)_p-C_3-C_3-C_7$cycloalkyl, or
 (f) 1- or 2-adamantyl;
wherein $R_{100}$ and $R_{101}$ taken together with the carbon atom and the nitrogen atom to which they are bonded to form -Het;
wherein $R_{102}$ is
 (a) hydrogen,
 (b) $C_1-C_7$alkyl,
 (c) $-(CH_2)_p$-aryl, (d) —(CH$_2$)$_p$-Het,
(e) —(CH$_2$)$_p$—C$_3$—C$_3$-C$_7$cycloalkyl,
(f) R$_5$—O—CH$_2$—C(O)—,
(g) R$_5$—CH$_2$—O—C(O)—,
(h) R$_5$—O—C(O)—,
(i) R$_5$—(CH$_2$)$_n$—C(O)—,
(j) R$_5$—(CH$_2$)$_n$—C(S)—,
(k) R$_4$N(R$_4$)—(CH$_2$)$_n$—C(O)—,
(l) R$_5$—SO$_2$—(CH$_2$)$_q$—C(O)—,
(m) R$_5$—SO$_2$—(CH$_2$)$_q$—O—C(O)— or
(n) R$_6$—(CH$_2$)$_i$—C(O)—;
(o) —[C(O)—AA—NH—]$_j$X;
wherein i is zero to five, inclusive;
wherein j is one to three, inclusive;
wherein m is one or two;
wherein for each occurrence n is independently an integer of zero to five, inclusive;
wherein p is zero to two, inclusive;
wherein q is one to five, inclusive;
wherein Q is
  (a) —CH$_2$—,
  (b) —CH(OH)—,
  (c) —O—, or
  (d) —S—;
wherein M is
  (a) —CO—, or
  (b) —CH$_2$—;
wherein aryl is phenyl or naphthyl substituted by zero to three of the following:
  (a) C$_1$-C$_3$alkyl,
  (b) hydroxy,
  (c) C$_1$-C$_3$alkoxy,
  (d) halo,
  (e) amino,
  (f) mono- or di-C$_1$-C$_3$alkylamino,
  (g) —CHO,
  (h) —COOH,
  (i) COOR$_{26}$,
  (j) CONHR$_{26}$,
  (k) nitro,
  (l) mercapto,
  (m) C$_1$-C$_3$alkylthio,
  (n) C$_1$-C$_3$alkylsulfinyl,
  (o) C$_1$-C$_3$alkylsulfonyl,
  (p) —N(R$_4$)—C$_1$-C$_3$alkylsulfonyl,
  (q) SO$_3$H,
  (r) SO$_2$NH$_2$,
  (s) —CN, or
  (t) —CH$_2$NH$_2$;
wherein -Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to three of the following:
  (i) C$_1$-C$_6$alkyl,
  (ii) hydroxy,
  (iii) trifluoromethyl,
  (iv) C$_1$-C$_4$alkoxy,
  (v) halo,
  (vi) aryl,
  (vii) aryl C$_1$-C$_4$alkyl-,
  (ix) mono- or di-(C$_1$-C$_4$alkyl)amino, and
  (x) C$_1$-C$_5$alkanoyl;
which nitrogen atom in the heterocyclic ring may be substituted with zero or one of the following:
  (a) HC(O),
  (b) t-butylcarbonyl,
  (c) benzyloxycarbonyl,
  (d) acetyl,
  (e) allyl,
  (f) phthalyl,
  (g) benzyl,
  (h) benzoyl, or
  (i) trityl;
or a carboxy-, amino-, or other reactive group-protected form thereof;
or a pharmaceutically acceptable acid addition salt thereof.

These peptides are useful as renin inhibitors and as inhibitors of retroviral proteases.

The present invention also provides the following novel intermediate compounds:

A peptide of the formula III
wherein X is
  (a) hydrogen,
  (b) C$_1$-C$_7$alkyl,
  (c) —(CH$_2$)$_p$-aryl,
  (d) —(CH$_2$)$_p$-Het,
  (e) —(CH$_2$)$_p$—C$_3$-C$_7$cycloalkyl,
  (f) R$_5$—O—CH$_2$—C(O)—,
  (g) R$_5$—CH$_2$—O—C(O)—,
  (h) R$_5$—O—C(O)—,
  (i) R$_5$—(CH$_2$)$_n$—C(O)—,
  (j) R$_5$—(CH$_2$)$_n$—C(S)—,
  (k) R$_4$N(R$_4$)—(CH$_2$)$_n$—C(O)—,
  (l) R$_5$—SO$_2$—(CH$_2$)$_q$—C(O)—,
  (m) R$_5$—SO$_2$—(CH$_2$)$_q$—O—C(O)— or
  (n) R$_6$—(CH$_2$)$_i$—C(O)—;
wherein A$_6$ is a divalent moiety of XL$_2$;
wherein B$_7$ is a divalent moiety of the formula XL$_b$;
wherein C$_8$ is a divalent moiety of the formula XL$_2$;
wherein R$_4$ at each occurrence is the same or different and is
  (a) hydrogen,
  (b) C$_1$-C$_5$alkyl.
  (c) —(CH$_2$)$_p$-aryl,
  (d) —(CH$_2$)$_p$-Het,
  (e) —(CH$_2$)$_p$—C$_3$-C$_7$cycloalkyl, or
  (f) 1- or 2-adamantyl;
wherein R$_5$ is
  (a) C$_1$-C$_6$alkyl.
  (b) C$_3$-C$_7$cycloalkyl,
  (c) aryl,
  (d) -Het, or
  (e) 5-oxo-2-pyrrolidinyl;
wherein R$_6$ is
  (a) hydrogen,
  (b) C$_1$-C$_5$alkyl.
  (c) —(CH$_2$)$_p$-aryl,
  (d) —(CH$_2$)$_p$-Het,
  (e) —(CH$_2$)$_p$—C$_3$-C$_7$cycloalkyl, or
  (f) 1- or 2-adamantyl;
wherein R$_{26}$ is
  (a) hydrogen,
  (b) C$_1$-C$_3$alkyl. or
  (c) phenyl-C$_1$-C$_3$alkyl;
wherein i is zero to five, inclusive;
wherein m is one or two;
wherein for each occurrence n is independently an integer of zero to five, inclusive;
wherein p is zero to two, inclusive;
wherein q is one to five, inclusive;
wherein Q is (a) —CH$_2$—,
(b) —CH(OH)—,
(c) —O—, or
(d) —S—;

wherein M is
(a) —CO—, or
(b) —CH$_2$—;

wherein aryl is phenyl or naphthyl substituted by zero to three of the following:
(a) C$_1$-C$_3$alkyl,
(b) hydroxy,
(c) C$_1$-C$_3$alkoxy,
(d) halo,
(e) amino,
(f) mono- or di-C$_1$-C$_3$alkylamino,
(g) —CHO,
(h) —COOH,
(i) COOR$_{26}$,
(j) CONHR$_{26}$,
(k) nitro,
(l) mercapto,
(m) C$_1$-C$_3$alkylthio,
(n) C$_1$-C$_3$alkylsulfinyl,
(o) C$_1$-C$_3$alkylsulfonyl,
(p) —N(R$_4$)—C$_1$-C$_3$alkylsulfonyl,
(q) SO$_3$H,
(r) SO$_2$NH$_2$,
(s) —CN, or
(t) —CH$_2$NH$_2$;

wherein —Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to three of the following:
(i) C$_1$-C$_6$alkyl,
(ii) hydroxy,
(iii) trifluoromethyl,
(iv) C$_1$-C$_4$alkoxy,
(v) halo,
(vi) aryl,
(vii) aryl C$_1$-C$_4$alkyl—,
(ix) mono- or di-(C$_1$-C$_4$alkyl)amino, and
(x) C$_1$-C$_5$alkanoyl;

which nitrogen atom in the heterocyclic ring may be substituted with zero or one of the following:
(a) HC(O)—,
(b) t-butylacaronyl,
(c) benzyloxycarbonyl,
(d) acetyl,
(e) allyl,
(f) phthalyl,
(g) benzyl,
(h) benzoyl, or
(i) trityl; and A compound of the formula XX
wherein R$_{200}$ is
(a) hydrogen,
(b) C$_1$-C$_7$alkyl,
(c) —(CH$_2$)$_p$-aryl,
(d) —(CH$_2$)$_p$-Het,
(e) —(CH$_2$)$_p$-C$_3$-C$_7$cycloalkyl,
(f) R$_5$—O—CH$_2$—C(O)—,
(g) R$_5$—CH$_2$—O—C(O)—,
(h) R$_5$—O—C(O)—,
(i) R$_5$—(CH$_2$)$_n$—C(O)—,
(j) R$_5$—(CH$_2$)$_n$—C(S)—,
(k) R$_4$N(R$_4$)—(CH$_2$)$_n$—C(O)—,
(l) R$_5$—SO$_2$—(CH$_2$)$_q$—C(O)—,
(m) R$_5$—SO$_2$—(CH$_2$)$_q$—O—C(O)—, or
(n) R$_6$—(CH$_2$)$_i$—C(O)—;

wherein R$_{300}$ and R$_{301}$ are the same or different and are:
(a) hydrogen,
(b) C$_1$-C$_7$alkyl,
(c) —(CH$_2$)$_p$-aryl,
(d) —(CH$_2$)$_p$-Het,
(e) —(CH$_2$)$_p$-C$_3$-C$_7$cycloalkyl, or
(f) 1- or 2-adamantyl;

wherein R$_{400}$ and R$_{401}$ taken together with the carbon atom and the nitrogen atom to which they are bonded to form -Het;

wherein R$_{402}$ is
(a) hydrogen,
(b) C$_1$-C$_7$alkyl,
(c) —(CH$_2$)$_p$-aryl,
(d) —(CH$_2$)$_p$-Het,
(e) —(CH$_2$)$_p$-C$_3$-C$_7$cycloalkyl,
(f) R$_5$—O—CH$_2$—C(O)—,
(g) R$_5$—CH$_2$—O—C(O)—,
(h) R$_5$—O—C(O)—,
(i) R$_5$—(CH$_2$)$_n$—C(O)—,
(j) R$_5$—(CH$_2$)$_n$—C(S)—,
(k) R$_4$N(R$_4$)—(CH$_2$)$_n$—C(O)—,
(l) R$_5$—SO$_2$—(CH$_2$)$_q$—C(O)—,
(m) R$_5$—SO$_2$—(CH$_2$)$_q$—O—C(O)—,
(n) R$_6$—(CH$_2$)$_i$—C(O)—,
(o) —[C(O)—AA—NH—]$_j$X$_1$, or
(p) —C≡N—C$_1$-C$_7$alkyl;

wherein aryl is phenyl or naphthyl substituted by zero to 3 of the following:
(a) C$_1$-C$_3$alkyl,
(b) hydroxy,
(c) C$_1$-C$_3$alkoxy,
(d) halo,
(e) amino,
(f) mono- or di-C$_1$-C$_3$alkylamino,
(g) —CHO,
(h) —COOH,
(i) COOR$_{26}$,
(j) CONHR$_{26}$,
(k) nitro,
(l) mercapto,
(m) C$_1$-C$_3$alkylthio,
(n) C$_1$-C$_3$alkylsulfinyl,
(o) C$_1$-C$_3$alkylsulfonyl,
(p) —N(R$_4$)—C$_1$-C$_3$alkylsulfonyl,
(q) SO$_3$H,
(r) SO$_2$NH$_2$,
(s) —CN, or
(t) —CH$_2$NH$_2$;

wherein -Het is a 5- or 6-membered saturated or unsaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to 3 of the following:
(i) C$_1$-C$_6$alkyl,
(ii) hydroxy,
(iii) trifluoromethyl,
(iv) C$_1$-C$_4$alkoxy,
(v) halo,
(vi) aryl, (vii) aryl $C_1$-$C_4$alkyl—,
(viii) amino,
(ix) mono- or di-($C_1$-$C_4$alkyl)amino, and
(x) $C_1$-$C_5$alkanoyl;
wherein $X_1$ is
  (a) hydrogen,
  (b) $C_1$-$C_7$alkyl,
  (c) —$(CH_2)_p$-aryl,
  (d) —$(CH_2)_p$-Het,
  (e) —$(CH_2)_p$—$C_3$-$C_7$cycloalkyl,
  (f) $R_5$—O—$CH_2$—C(O)—,
  (g) $R_5$—$CH_2$—O—C(O)—,
  (h) $R_5$—O—C(O)—,
  (i) $R_5$—$(CH_2)_n$—C(O)—,
  (j) $R_5$—$(CH_2)_n$—C(S)—,
  (k) $R_4N(R_4)$—$(CH_2)_n$—C(O)—,
  (l) $R_5$—$SO_2$—$(CH_2)_q$—C(O)—,
  (m) $R_5$—$SO_2$—$(CH_2)_q$—O—C(O)— or
  (n) $R_6$—$(CH_2)_i$—C(O)—;
wherein $R_4$ at each occurrence is the same or different and is
  (a) hydrogen,
  (b) $C_1$-$C_5$alkyl,
  (c) —$(CH_2)_p$-aryl,
  (d) —$(CH_2)_p$-Het,
  (e) —$(CH_2)_p$—$C_3$-$C_7$ cycloalkyl, or
  (f) 1- or 2-adamantyl;
wherein $R_5$ is
  (a) $C_1$-$C_6$alkyl,
  (b) $C_3$-$C_7$cycloalkyl,
  (c) aryl,
  (d) -Het, or
  (e) 5-oxo-2-pyrrolidinyl;
wherein $R_6$ is
  (a) hydrogen,
  (b) $C_1$-$C_5$alkyl,
  (c) —$(CH_2)_p$-aryl,
  (d) —$(CH_2)_p$-Het,
  (e) —$(CH_2)_p$—$C_3$-$C_7$cycloalkyl, or
  (f) 1- or 2-adamantyl;
wherein $R_{26}$ is
  (a) hydrogen,
  (b) $C_1$-$C_3$alkyl, or
  (c) phenyl-$C_1$-$C_3$alkyl;
wherein i is zero to five, inclusive;
wherein j is one to three, inclusive;
wherein for each occurrence n is independently an integer of zero to five, inclusive;
wherein p is zero to two, inclusive;
wherein q is one to five, inclusive, By —[C(O)—AA—NH—]$_j$X is meant an amino acid residue including the naturally-ocurring amino acids such as: glycine, alanine, valine, leucine, isoleucine, phenylalanine, lysine, proline, tryptophan, methionine, serine, threonine, cysteine, tyrosine, asparagine, glutamine, aspartic acid, glutamic acid, arginine, ornithine, and histidine, and synthetic derivatives thereof. These compounds may be in L or D configuration and are well known and readily available to those skilled in the art. In this formula, j is an integer from one to three, inclusive, so that two or three amino acid residues may be joined to yield a dipeptide or a tripeptide, respectively, and X is a terminal group.

The amino acid derivatives may be in the "D" and/or "L" configuration, the prefixes "D" and "L" being a means of indicating the relative configurations of various optically active compounds, especially carbohydrates. The compound glyceraldehyde, $CH_2OH$-CHOHCHO, was selected as a standard of reference, because it is the simplest carbohydrate—an aldotriose—capable of optical isomerism. (+)-Glyceraldehyde was arbitrarily assigned a configuration and was designated D-glyceraldehyde, and (−)-glyceraldehyde was assigned a second configuration and was designated L-glyceraldehyde. R. T. Morrison and R. N. Boyd, Organic Chemistry, 1087-88 (1978). Compounds related configuationally to D-glyceraldehyde are given the designation D, and compounds related to L-glyceraldehyde are given the designation L. Organic Chemistry at 1089.

By "renin inhibitory peptide" is meant a compound capable of inhibiting the renin enzyme in mammalian metabolism and having three or more amino acid residues linked by peptidic or pseudo-peptidic bonds.

By "a non-cleavable transition state insert" is meant a transition state insert which is not cleavable by a hydrolytic enzyme in mammalian metabolism. A variety of such transition state inserts, corresponding to the 10,11-position of the renin substrate, are known in the art, including those disclosed in the following references:

U.S. Pat. No. 4,424,207 (Szelke); European Patent 104041A (Szelke); European Patent Application 144,290A (Ciba Geigy AG); European Patent 0,156,322 (Merck); European Patent 161-588A (Merck); European Patent 0,172,347 (Abbott); European Patent 172-346-A (Abbott); European Patent 156-318 (Merck); European Patent 157-409 (Merck); European Patent 152-255 (Sankyo); and U.S. Pat. No. 4,548,926 (Sankyo); and U.S. patent application Ser. No. 904,149, filed Sep. 5, 1986; U.S. patent application Ser. No. 844,716, filed Mar. 27, 1986; PCT application, Ser. No. 000,713, filed Apr. 7, 1986; U.S. patent application Ser. No. 945,340, filed Dec. 22, 1986; and U.S. patent application Ser. No. 825,250, filed Feb. 3, 1986; and A. Spaltenstein, P. Carpino, F. Miyake and P. B. Hyskins, Tetrahedron Letters, 27:2095 (1986); D. H. Rich and M. S. Bernatowicz, J. Med. Chem., 25:791 (1982); Roger, J. Med. Chem., 28:1062 (1985); D. M. Glick et al., Biochemistry, 21:3746 (1982); D. H. Rich, Biochemistry, 24:3165 (1985); R. L. Johnson, J. Med. Chem., 25:605 (1982); R. L. Johnson and K. Verschovor. J. Med. Chem., 26:1457 (1983); R. L. Johnson, J. Med. Chem., 27:1351 (1984); P. A. Bartlett et al., J. Am. Chem. Soc., 106:4282 (1984); and Peptides: Synthesis, Structure and Function (V. J. Hruby; D. H. Rich, eds.) Proc. 8th American Peptide Sym., Pierce Chemical Company, Rockford, Ill., pp. 511-20; 587-590 (1983).

As is apparent to those of ordinary skill in the art, the peptides of the present invention can occur in several isomeric forms, depending on the configuration around the asymmetric carbon atoms. All such isomeric forms are included within the scope of the present invention. The E isomer of the cyclopropyl amino acid is preferred. Preferably, the stereochemistry of the other amino acids corresponds to that of the naturally-occurring amino acids.

Renin inhibitory peptides commonly have protecting groups at the N-terminus and the C-terminus. These protecting groups are known in the polypeptide art. Examples of these protecting groups are given below. Any of these protecting groups are suitable for the peptides of the present invention.

Preferably, the moiety of the formula $XL_{2c}$ of the present invention may occur at the C-terminus of the peptide and, as such, will, when coupled with a suitable protecting group, assume the ending position.

These compounds are shown in relation to the human renin substrate as follows:

```
    6    7    8    9   10   11   12   13
  —His  Pro  Phe  His  Leu  Val  Ile  His—
X   A₆   B₇   C₈   D₉   E₁₀  F₁₁  G₁₂  H₁₃  I₁₄  Z,
```

The present invention provides peptide inhibitors of renin and retroviral proteases which contain the moiety of the formula $XL_{2c}$.

Examples of pharamaceutically acceptable acid addition salts include: acetate, adipate, alginate, asparate, benzoate, benzenesulfonate, bisulfate, butyrate, citrate, camphorate, camphorsulfonate, cyclopentanepropionate, digluconate, dodecylsulfate, ethanesulfonate, fumarate, glucoheptanoate, glycerophosphate, hemisulfate, heptanoate, hexanoate, hydrochloride, hydrobromide, hydroiodide, 2-hydroxyethanesulfonate, lactate, maleate, methansulfonate, 2-naphthalenesulfonate, nicotinate, oxalate, palmoate, pectinate, persulfate, 3-phenylpropionate, picrate, pivalate, propinoate, succinate, tartrate, thiocyanate, tosylate, and undecanoate.

The carbon atom content of various hydrocarbon-containing moieties is indicated by a prefix designating the minimum and maximum number of carbon atoms in the moiety, i.e., the prefix $(C_i-C_j)$ indicates a moiety of the integer "i" to the integer "j" carbon atoms, inclusive. Thus $(C_1-C_4)$alkyl refers to alkyl of one to 4 carbon atoms, inclusive, or methyl, ethyl, propyl, butyl, and isomeric forms thereof. $C_4-C_7$cyclic amino indicates a monocyclic group containing one nitrogen and 4 to 7 carbon atoms.

Examples of $(C_3-C_{10})$cycloalkyl which include alkyl-substituted cycloalkyl containing a total of up to 10 total carbon atoms, are cyclopropyl, 2-methylcyclopropyl, 2,2-dimethylcyclopropyl, 2,3-diethylcyclopropyl, 2-butylcyclopropyl, cyclobutyl, 2-methylcyclobutyl, 3-propylcyclobutyl, cyclopentyl, 2,2-dimethylcyclopentyl, cyclohexyl, cycloheptyl, cyclooctyl, cyclononyl, cyclodecyl and isomeric forms thereof.

Examples of aryl include phenyl, naphthyl, (o-, m-, p-)tolyl, (o-, m-, p-)ethylphenyl, 2-ethyl-tolyl, 4-ethyl-o-tolyl, 5-ethyl-m-tolyl, (o-, m-, or p-)propylphenyl, 2-propyl-(o-, m-, or p-)tolyl, 4-isopropyl-2,6-xylyl, 3-propyl-4-ethylphenyl, (2,3,4- 2,3,6-, or 2,4,5-)-trimethylphenyl, (o-, m-, or p-)fluorophenyl, (o-, m-, or p-trifluoromethyl)phenyl, 4-fluoro-2,5-xylyl, (2,4-, 2,5-, 2,6-, 3,4-, or 3,5-)difluorophenyl, (o-, m-, or p-)chlorophenyl, 2-chloro-p-tolyl, (3-, 4-, 5- or 6-)chloro-o-tolyl, 4-chloro-2-propylphenyl, 2-isopropyl-4-chlorophenyl, 4-chloro-3-fluorophenyl, (3- or 4-)chloro-2-fluorophenyl, (o-, m-, or p-)trifluoro-methylphenyl, (o-, m-, or p-)ethoxyphenyl, (4- or 5-)chloro-2-methoxy-phenyl, and 2,4-dichloro-(5- or 6-)methylphenyl, and the like.

Examples of -Het include: 2-, 3-, or 4-pyridyl, imidazolyl, indolyl, $N^{in}$-formyl-indolyl, $N^{in}$-$C_1$-$C_5$alkyl-C(O)-indolyl, [1,2,4]-triazolyl, 2-, 4-, or 5-pyrimidinyl, 2- or 3-thienyl, piperidinyl, pyrryl, pyrrolinyl, pyrrolidinyl, pyrazolyl, pyrazolinyl, pyrazolidinyl, imidazolinyl, imidazolidinyl, pyrazinyl, piperazinyl, pyridazinyl, oxazolyl, oxazolidinyl, isoxazolyl, isoxazolidinyl, morpholinyl, thiazolyl, thiazolidinyl, isothiazolyl, isothiazolidinyl, quinolinyl, isoquiniolinyl, benzimidazolyl, benzothiazolyl, benzoxazolyl, furyl, thienyl, and benzothienyl. Each of these moieties may be substituted as noted above.

As would be generally recognized by those skilled in the art of organic chemistry, a heterocycle as defined herein for -Het would not be bonded through oxygen or sulfur or through nitrogen which is within a ring and part of a double bond.

Halo is halogen (fluoro, chloro, bromo, or iodo) or trifluoromethyl.

Examples of pharmaceutically acceptable cations include: pharmacologically acceptable metal cations, ammonium, amine cations, or quaternary ammonium cations. Especially preferred metal cations are those derived from the alkali metals, e.g., lithium, sodium, and potassium, and from the alkaline earth metals, e.g., magnesium and calcium, although cationic forms of other metals, e.g., aluminum, zinc, and iron are also within the scope of this invention. Pharmacologically acceptable amine cations are those derived from primary, secondary, or tertiary amines.

The novel peptides herein contain both natural and synthetic amino acid residues. These residues are depicted using standard amino acid abbreviations (see, e.g., Eur. J. Biochem., 138, 9 (1984)) unless othewise indicated.

In addition to the treatment of warm-blooded animals such as mice, rats, horses, dogs, cats, etc., the compounds of the invention are effective in the treatment of humans.

The peptides of this invention are useful for treating any medical condition which it is beneficial to reduce the levels of active circulating renin. Examples of such cnditions include renin-associated hypertension and hyperaldosteronism, hypertension, hypertension under treatment with another antihypertensive and/or a diuretic agent, congestive heart failure, angina and post-myocardial infarction. The renin-angiotension system may play a role in maintenace of intracellular homeostasis: see Clinical and Experimental Hypertension, 86, 1739-1742 (1984) at page 1740 under Discussion. The peptides will also be useful as molecular probes for the diagnosis and study of the physiology of blood pressure regulation or other physiological functions.

Further, the peptides of this invention may be useful in the treatment of cerebrovascular disorders and disorders of intracellular homeotasis. The possible role of the renin-angiotensin system in the maintenance of intracellular homeostasis is disclosed in Clinical and Experimental Hypertension, 86:1739-1742 (1984). Additionally, the peptides of this invention potentiate the antithrombotic activity of a thromboxane antagonist (U.S. Pat. No. 4,558,037). The antihypertensive effect of the peptides of this invention are potentiated by combination with a thromboxane synthetase inhibitor.

The peptides of the present invention are preferably orally administered to humans to effect renin inhibition for the purpose of favorably affecting blood pressure. For this purpose, the peptides are administered from 0.1 mg to 1000 mg per kg per dose, administered from 1 to 4 times daily. The peptides of the present invention are preferably orally administered in the form of pharmacologically acceptable acid addition salts. Preferred pharmacologically acceptable salts for oral administration include the citrate and aspartate salts, although any pharmacologically acceptable salt is useful in this invention, including those listed above. These salts may be in hydrated or solvated form.

Other routes of administration include parenteral, by inhalation spray, or rectally in dosage unit formulations containing conventional non-toxic pharmaceutically acceptable carriers, adjuvants and vehicles. The term parenteral as used herein includes subscutaneous injections, intravenous, intramuscular, intrasternal injection or infusion techniques.

The pharmaceutical compositions of the peptides of the present invention may be in the form of a sterile injectable preparation, for example as a sterile injectable aqueous or oleagenous suspension. This suspension may be formulated according to the known art using suitable dispersing or wetting agents and suspending agents. The sterile injectable preparation may also be a sterile injectable solution or suspension in a non-toxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose any bland fixed oil may be employed including synthetic mono- or diglycerides. In addition, fatty acids such as oleic acid find use in the preparation of injectibles.

Equivalent dosages for such other routes of administration are thus employed. The exact dose depends on the age, weight, and condition of the patient and on the frequency and route of administration. Such variations are within the skill of the practitioner or can readily be determined.

The peptides of the present invention may be in the form of pharmaceutically acceptable salts both those which can be produced from the free bases by methods well known in the art and those with which acids have pharmacologically acceptable conjugate bases.

Conventional forms and means for administering renin-inhibiting compounds may be employed and are described, e.g., in U.S. Pat. No. 4,424,207 which is incorporated by reference herein. Likewise, the amounts disclosed in the U.S. Pat. No. 4,424,207 are examples applicable to the peptides of the present invention.

The peptides of this invention to effect renin inhibition may be administered in combination with other agents used in antihypertensive therapy such as diuretices, $\alpha$ and/or $\beta$-adrenergic blocking agents, CNS-acting agents, adrenergic neuron blocking agents, vasodilators, angiotensin I converting enzyme inhibitors, and the like as described, for example, in published European patent application 156 318.

For example, the peptides of this invention can be given in combination with such compounds or salts or other derivative forms thereof as:

Diuretics: acetazolamide; amiloride, bendroflumethiazide; benzthiazide; bumetanide; chlorothiazide; chlorthalidone; cyclothiazide; ethacrynic acid; furosemide; hydrochlorothiazide; hydroflumethiazide; indacrinone (racemic mixture, or as either the (+) or (−) enantiomer alone, or a manipulated ratio, e.g., 9:1 of said enantiomers, respectively); metolazone; methyclothiazide; muzolimine; polythiazide; quinethazone; sodium ethacrynate; sodium nitroprusside; spironolactone; ticrynaten; trimaterene; trichlormethiazide;

$\alpha$-Adrenergic Blocking Agents: dibenamine; phentolamine; phenoxybenzamine; prazosin; tolazoline;

$\beta$-Adrenergic Blocking Agents: atenolol; metoprolol; nadolol; propranolol; timolol;

(($\pm$)-2-[3-(tert-butylamino)-2-hydroxypropoxy]-2-furananilide) (ancarolol);

(2-acetyl-7-(2-hydroxy-3-isopropylaminopropoxy)benzofuran HCl) (befunolol);

(($\pm$)-1-(isopropylamino)-3-(p-(2-cyclopropylmethoxyethyl)-phenoxy)-2-propanol HCl) (betaxolol);

(1-[(3,4-dimethoxyphenethyl)amino]-3-(m-tolyloxy)-2-propanol HCl) (beventolol);

((($\pm$)-1-(4-((2-isopropoxyethoxy)methyl)phenoxy)-3-isopropylamino-2-propanol)fumarate) (bisoprolol);

(4-(2-hydroxy-3-[4-(phenoxymethyl)-piperidino]-propoxy)-indole);

(carbazolyl-4-oxy-5,2-(2-methoxyphenoxy)-ethylamino-2-propanol);

(1-((1,1-dimethylethyl)amino)-3-((2-methyl 'H-indol-4-yl)oxy)-2-propanol benzoate) (bopindolol);

(1-(2-exobicyclo[2.2.1]-hept-2-ylphenoxy)-3-[(1-methylethyl)-amino]-2-propanol HCl) (bornaprolol);

(o-[2-hydroxy-3-[(2-indol-3-yl-1,1-dimethylethyl)-amino]propoxy]benzonitrile HCl) (bucindolol);

($\alpha$-[(tert.butylamino)methyl]-7-ethyl-2-benzofuranmethanol) (bufuralol);

(3-[3-acetyl-4-[3-(tert.butylamino)-2-hydroxypropyl]-phenyl]-1,1-diethylurea HCl) (celiprolol);

(($\pm$)-2-[2-[3-[(1,1-dimethylethyl)amino[-2-hydroxypropoxy]phenoxy]-N-methylacetamide HCl) (cetamolol);

(2-benzimidazolyl-phenyl(2-isopropylaminopropanol));

(($\pm$)-3'-acetyl-4'-(2-hydroxy-3-isopropylaminopropoxy)-acetanilide HCl) (diacetolol);

(methyl-4-[2-hydroxy-3-[(1-methylethyl)aminopropoxyl]]-benzenepropanoate HCl) (esmolol);

(erythro-DL-1-(7-methylindan-4-yloxy)-3-isopropylaminobutan-2-ol);

(1-(tert.butylamino)-3-[0-(2-propynyloxy)phenoxy]-2-propanol (pargolol);

(1-(tert.butylamino)-3-[o-(6-hydrazino-3-pyridazinyl)-phenoxy[-2-propanol diHCl) (prizidilol);

((−)-2-hydroxy-5-[(R)-1-hydroxy-2-[(R)-(1-methyl-3-phenylpropyl)-amino]ethyl]benzamide);

(4-hydroxy-9-[2-hydroxy-3-(isopropylamino)-propoxy]-7-methyl-5H-furo[3,2-g][1]-benzopyran-5-one) (iprocrolol);

((−)-5-(tert.butylamino)-2-hydroxypropoxy]-3,4-dihydro-1-(2H)-naphthalenone HCl) (levobunolol);

(4-(2-hydroxy-3-isopropylamino-propoxy)-1,2-benzisothiazole HCl);

(4-[3-(tert.butylamino)-2-hydroxypropoxy]-N-methylisocarbostyril HCl);

(($\pm$)-N-2-[4-(2-hydroxy-3-isopropylaminopropoxy)-phenyl]ethyl-N'-isopropylurea) (pafenolol);

(3-[[(2-trifluoroacetamido)ethyl]amino]-1-phenoxypropan-2-ol);

(N-(3-(o-chlorophenoxy)-2-hydroxypropyl)-N'-(4'-chloro-2,3-dihydro-3-oxo-5-pyridazinyl)ethylenediamine);

(($\pm$)-N-[3-acetyl-4-[2-hydroxy-3-[(1-methylethyl)amino]propoxyphenyl]-butanamide) (acebutolol);

(($\pm$)-4'-[3-(tert-butylamino)-2-hydroxypropoxy]spiro[cyclohexane-1,2'-indan]-1'-one) (spirendolol);

(7-[3-[[2-hydroxy-3-[(2-methylindol-4-yl)oxylpropyl]amino]butyl]thiophylline) (teoprolol);

(($\pm$)-1-tert.butylamino-3-(thiochroman-8-yloxy)-2-propanol) (tertatolol);

(($\pm$)-1-tert.butylamino-3-(2,3-xylyloxy)-2-propanol HCl) (xibenolol);

(8-[3-(tert.butylamino)-2-hydroxypropoxy]-5-methylcoumarin) (bucumolol);

(2-(3-(tert.butylamino)-2-hydroxy-propoxy)benzonitrile HCl) (bunitrolol);

(($\pm$)-2'-[3-(tert.butylamino)-2-hydroxypropoxy-5'-fluorobutyrophenone) (butofilolol);

(1-(carbazol-4-yloxy)-3-(isopropylamino)-2-propanol) (carazolol);
(5-(3-tert.butylamino-2-hydroxy)propoxy-3,4-dihydrocarbotyril HCl) (carteolol);
(1-(tert.butylamino)-3-(2,5-dichlorophenoxy)-2-propanol) (cloranolol);
(1-(inden-4(or 7)-yloxy)-3-(isopropylamino)-2-propanol HCl) (indenolol);
(1-isopropylamino-3-[(2-methylindol-4-yl)oxy]-2-propanol) (mepindolol);
(1-(4-acetoxy-2,3,5-trimethylphenoxy)-3-isopropylaminopropan-2-ol) (metipranolol);
(1-(isopropylamino)-3-(o-methoxyphenoxy)-3[(1-methylethyl)amino]-2-propanol) (moprolol);
((1-tert.butylamino)-3-[(5,6,7,8-tetrahydro-cis-6,7-dihydroxy-1-napthyl)oxy]-2-propanol) (nadolol);
((S)-1-(2-cyclopentylphenoxy)-3-[(1,1-dimethylethyl)amino[-2-propanol sulfate (2:1)) (penbutolol);
(4'-[1-hydroxy-2-(amino)ethyl]methanesulfonanilide) (sotalol);
(2-methyl-3-[4-(2-hydroxy-3-tert.butylaminopropoxy)-phenyl]-7-methoxyisoquinolin-1-(2H)-one);
(1-(4-(2-(4-fluorophenyloxy)ethoxy)phenoxy)-3-isopropylamino-2propanol HCl);
((−)-p-[3-[(3,4-dimethoxyphenethyl)amino[2-hydroxy-propoxy]-β-methylcinnamonitrile) (pacrinolol);
((±)-2-(3'-tert.butylamino-2'-hydroxypropylthio)-4-(5'-carbamoyl-2'-thienyl)thiazole HCl) (arotinolol);
((±)-1-[p-[2-(cyclopropylmethoxy)ethoxy]ethoxy]phenoxy]-3-(isopropylamino)-2-propanol) (cicloprolol);
((±)-1-[(3-chloro-2-methylindol-4-yl)oxy]-3-[(2-phenoxyethyl)amino]-2-propanol) (indopanolol);
((±)-6-[[2-[[3-(p-butoxyphenoxyl)-2-hydroxypropyl]amino]ethyl]amino]-1,3-dimethyluracil) (pirepolol);
(4-(cyclohexylamino)-1-(1-naphtholenyloxy)-2-butanol);
(1-phenyl-3-[2-[3-(2-cyanophenoxy)-2-hydroxypropyl]aminoethyl]hydrantion HCl);
(3,4-dihydro-8-(2-hydroxy-3-isopropylaminopropoxy)-3-nitroxy-2H-1-benzopyran) (nipradolol);

Angiotensin I Converting Enzyme Inhibitors
1-(3-mercapto-2-methyl-1-oxopropyl)-L-proline (captopril);
(1-(4-ethoxycarbonyl-2,4(R,R)-dimethlbutanoyl)indoline-2(S)-carboxylic acid);
(2-[2-[(1-(ethoxycarbonyl))-3-phenyl-propyl]amino]-1-oxopropyl]-1,2,3,4-tetrahydro-3-isoquinoline carboxylic acid);
((S)-1-[2-[(1-(ethoxycarbonyl)-3-phenylpropyl]amino]-1-oxopropyl]octahydro-1H-indole-2-carboxylic acid HCl);
(N-cyclopentyl-N-(3-(2,2-dimethyl-1-oxopropyl)thiol-2-methyl-1-oxopropyl)glycine) (pivalopril);
((2R,4R)-2-(2-hydrophenyl)-3-(3-mercaptopropionyl)-4-thiazolidinecarboxylic acid);
(1-(N-[1(S)-ethoxycarbonyl-3-phenylpropyl]-(S)-alanyl)-cis,syn-octahydroindol-2(S)-carboxylic acid HCl);
((−)-(S)-1-[(S)-3-mercapto-2-methyl-1-oxopropyl]indoline-2-carboxylic acid);
([1(S),4S[-1-[3-(benzoylthio)-2-methyl-1-oxopropyl]-4-phenylthio-L-proline;
(3-([1-ethoxycarbonyl-3-phenyl-(1S)-propyl]amino)-2,3,4,5-tetrahydro-2-oxo-1-(3S)-benzazepine-1-acetic acid HCl);
(N-(2-benzyl-3-mercaptopropanoly)-S-ethyl-L-cysteine) and the S-methyl analogue;
(N-(1(S)-ethoxycarbonyl-3-phenylpropyl)-L-alanyl-L-proline maleate) (enalapril);
N-[1-(S)-carboxy-3-phenylpropyl[-L-alanyl-1-proline;
$N^2$-[1-(S)-carboxy-3-phenylpropyl[-L-lysyl-L-proline (lysinopril);

Other Antihypertensive Agents: aminophylline; cryptenamine acetates and tannates; deserpidine; meremethoxylline procaine; pargyline; tri-methaphan camsylate; and the like, as well as admixtures and combinations thereof.

Typically, the individual daily dosages for these combinations can range from about one-fifth of the minimally recommended clinical dosages to the maximum recommended levels for the entities when they are given singly. Coadministration is most readily accomplished by combining the active ingredients into a suitable unit dosage form containing the proper dosages of each. Other methods of coadiminstration are, of course, possible.

Thus, the novel peptides of the present invention possess an excellent degree of activity in treating renin-associated hypertension and hyperaldosteronism.

Renin inhibitors have also been disclosed to control the rise in intraocular pressure associated with the use of steroidal anti-inflammatory drugs as described in International Application PCT/-U.S.86/02291 (International Publication Number WO 87/02581 dated 7 May 1987).

The peptides of the present invention are also useful as novel human retroviral protease inhibitory peptide analogs. Therefore, the peptides of the present invention inhibit retroviral proteases and thus inhibit the replication of the virus. They are useful for treating human patients infected with a human retrovirus, such as human immunodeficiency virus (HIV) which results in acquired immunodeficiency disease syndrome (AIDS) and related diseases.

The capsid and nonstructural proteins of retroviruses are translated from the viral genes gag and pol as polyproteins that are further processed by the viral protease (PR) to the mature proteins found in the viral capsid and necessary for viral functions and replication. If the PR is absent or nonfunctional, the virus cannot replicate. The retroviral PR, such as HIV-1 PR, has been found to be an aspartic protease with active site characteristics similar to those exhibited by the more complex aspartic protease, renin.

The term human retrovirus (HRV) includes human immunodeficiency virus type I, human immunodeficiency virus type II, or strains thereof, as well as human T cell leukemia virus 1 and 2 (HTLV-1 and HTLV-2) or strains apparent to one skilled in the art, which belong to the same or related viral families and which create similar physiological effects in humans as various human retroviruses.

Patients to be treated would be those individuals: 1) infected with one or more strains of a human retrovirus as determined by the presence of either measurable viral antibody or antigen in the serum and 2) having either a symptomatic AIDS defining infection such as i) disseminated histoplasmosis, ii) isopsoriasis, iii) bronchial and pulmonary candidiasis including pneumocystic pneumonia iv) non-Hodgkin's lymphoma or v) Kaposi's sarcoma and being less than sixty years old; or having an absolute CD4 lymphocyte count of less than 200/m$^3$ in the peripheral blood. Treatment would consist of maintaining an inhibitory level of the peptide used according to this invention in the patient at all times and would continue until the occurrence of a second symptomatic AIDS defining infection indicates alternate therapy is needed.

More specifically, an example of one such human retrovirus is the human immunodeficiency virus (HIV, also known as HTLV-III or LAV) which has been recognized as the causative agent in human acquired immunodeficiency disease syndrome (AIDS), P. Duesberg, Proc. Natl. Acad. Sci. USA, 86:755 (1989). HIV contains a retro viral encoded protease, HIV-I protease, that cleaves the fusion polypeptides into the functional proteins of the mature virus particle, E. P. Lillehoj, et al., J. Virology, 62:3053 (1988); C. Debuck, et al., Proc. Natl. Acad. Sci., 84:8903 (1987). This enzyme, HIV-I protease, has been classified as an aspartyl protease and has a demonstrated homology to other aspartyl proteases such as renin, L. H. Pearl, et al., Nature 328:351 (1987); I. Katoh, et al., Nature 329:654 (1987). Inhibition of HIV-I protease blocks the replication of HIV and thus is useful in the treatment of human AIDS, E. D. Clerq. J. Med. Chem. 29:1561 (1986). Inhibitors of HIV-I protease are useful in the treatment of AIDS.

Pepstatin A, a general inhibitor of aspartyl proteases, has been disclosed as an inhibitor of HIV-I protease, S. Seelmeier, et al., Proc. Natl. Acad. Sci. USA, 85:6612 (1986). Other substrate derived inhibitors containing reduced bond isosteres or statine at the scissle position have also been disclosed, M. L. Moore, et al., Biochem. Biophys, Res. Commn. 159:420 (1989); S. Billich, et al., J. Biol. Chem. 263:17905 (1988); Sandoz, D. E. 3812-576-A.

Thus, the peptides of the present invention are useful for treating diseases caused by retroviruses, such as human acquired immunodeficiency disease syndrome (AIDS), using dosages, forms and modes of administration equivalent to those described above for renin inhibition. Exact dosages, forms and mode of administration would be apparent to one of ordinary skill in the art such as a physician or pharamacologist.

The compounds of the present invention are prepared as depicted in the charts and as described more fully in the Preparations and Examples. In the charts, Boc represents butyloxycarbonyl; Cbz represents benzyloxycarbonyl; Ph represents phenyl.

CHART A

The synthesis of the compounds of formula A-3 and A-4 is shown in Chart A. Addition of the aldehyde of formula A-1, preparation of which is known in the art, to a twofold excess of the lithiated pyrrolidine formamide of formula A-2, prepared as described in A. I. Meyers et al., J. Amer. Chem. Soc., 106:3270–3276 (1984), in tetrahydrofuran at −80° C. affords a mixture of two diastereomeric alcohols of formula A-3 and A-4. While inspection of the crude reaction by NMR clearly indicates a preference for the formation of the threo diastereomer, the alcohol of formula A-3 (2/1), purification (silica gel) always affords an approximate 1/1 mixture of the diastereomeric alcohols. The alcohol of formula A-3 is a viscous oil while the alcohol of formula A-4 is a crystalline solid. The alcohols of formula A-3 and A-4 are used as the starting materials for the compounds prepared in Charts B and C.

CHART B

The synthesis of the compound of formula B-7 is shown in Chart B. The compound of formula A-3, prepared as described in Chart A, is used as the formula B-1 starting material. Treatment of the compound of formula B-1 with hydrazine in acidic aqueous ethanol as described by Meyers et al., J. Am. Chem. Soc. (1984) 106, 3270–76, affords the desired Boc-amino alcohol of formula B-2 as a white solid. The Boc-amino alcohol of formula B-2 is then converted to the Boc-Cbz alcohol of formula B-3. Treatment of the Boc-Cbz alcohol of formula B-3 with trifluoroacetic acid/methylene chloride (0° C.) then affords the amino alcohol of formula B-4 which is coupled to histidine. Addition of triethylamine (TEA) to a mixture of Boc-L-His($\pi$Bom)-OH, the amino alcohol of formula B-4, and diethylphosphorylcyanide (DEPC) in dimethylformamide (DMF) affords the desired pseudo dipeptide of formula B-5. Since racemization may occur at either the oxidation step (alcohol to aldehyde) and/or the addition of the lithiated pyrrolidine formamide of formula A-2 to the aldehyde of formula A-1 (see Chart A), the dipeptide of formula B-5 is an approximate 2:1 mixture of diastereomers (11 and d1). The dipeptide of formula B-5 is then debocylated with 50% trifluoroacetic acid (TFA)/methylene chloride at 0° C. The resulting amine is coupled to Ac-Trp[$N^{in}$-For]-Pro-Phe-OH using diethylphosphorylcyanide (DEPC) as the coupling reagent to yield the compound of formula B-6 as crude material. The compound of formula B-6 is then treated with anhydrous hydrogen fluoride to remove the benzyloxycarbonyl (Cbz) and the benzoyoxymethyl protecting groups to afford, after purification, the desired peptide of formula B-7 as the trifluoroacetate (TFA) salt.

CHART C

The synthesis of the diastereomeric compounds of formula C-7 and C-8 is shown in Chart C. The compound of formula A-4, prepared as described in Chart A, is used as the formula C-1 starting material. Treatment of the compound of formula C-1 with hydrazine in acidic aqueous ethanol as described by Meyers et al., J. Am. Chem. Soc. (1984) 106, 3270–76, affords the desired Boc-amino alcohol of formula C-2. The Boc-amino alcohol of formula C-2 is then converted to the Boc-Cbz alcohol of formula C-3. Treatment of the Boc-Cbz alcohol of formula C-3 with trifluoroacetic acid/methylene chloride then affords the amino alcohol of formula C-4. Addition of triethylamine (TEA) to a mixture of Boc-L-His($\pi$Bom)-OH, the amino alcohol of formula C-4, and diethylphosphorylcyanide (DEPC) in dimethylformamide (DMF) affords the desired pseudo dipeptide of formula C-5. As in the case of the dipeptide of formula B-5, the dipeptide of formula C-5 is also an approximate 2:1 mixture of diastereomers (11 and d1). The dipeptide of formula C-5 is then debocylated with trifluoroacetic acid (TFA)/methylene chloride (0° C.), and coupled to Ac-Trp[$N^{in}$-For]-Pro-Phe-OH using diethylphosphorylcyanide (DEPC) as the coupling agent to yield the compound of formula C-6 as crude material. The compound of formula C-6 is then treated with anhydrous hydrogen fluoride to remove the benzyloxycarbonyl (Cbz) and the benzyloxymethyl protecting groups to afford, after purification, two diastereomeric peptides of formula C-7 and C-8.

Other peptides of the present invention, which contain a moiety of the formula $XL_{2c}$ wherein $R_{90}$, $R_{91}$, $R_{100}$, $R_{101}$ and $R_{102}$ are as defined above, may be prepared by processes analogous to those described in Charts A, B and C by using the appropriate starting materials.

Aldehydes of the formula V bearing the desired $R_{90}$ and $R_{91}$ groups may be obtained from the corresponding natural and unnatural protected amino acids and esters by procedures known in the art.

Lithiated heterocyclic compounds of the formula VI, wherein n is o or 1 to form aromatic, unsaturated and saturated compounds, wherein $R_{100}$ and $R_{101}$ taken together with the carbon and nitrogen atoms to which they are bonded to form the desired heterocyclic ring and wherein $R_{102}$ is a cleavable protecting group, may be prepared by processes analogous to those described in P. Beak, Chem. Review, 84:471–523 (1984); and Handbook of Heterocyclic Compounds, Ed. A. R. Katritzky, Pergamon Press, Oxford (1985), p. 261. Such protecting groups include carbamates, aryl or alkyl amides, thioamides, ureas and formamidine. Formamidine is the preferred protecting group. When there is one heteroatom in the heterocyclic ring, lithiation occurs on the carbon atom of the ring adjacent to the heteroatom. When there is more than one heteroatom in the heterocyclic ring, lithiation occurs at the carbon atom of the ring adjacent to the heteroatom which has been activated for metallation. See, for example, P. Beak, Chem. Review, 84:471–523 (1984); A. I. Meyers et al., J. Amer. Chem. Soc., 106:3270–3276 (1984).

Taking the appropriate aldehyde and heterocyclic compounds as starting materials and using the procedures described in Charts A, B and C, other peptides of the present invention may be prepared.

Likewise, the intermediate compound of the formula XX, wherein $R_{200}$, $R_{300}$, $R_{301}$, $R_{400}$, $R_{401}$, and $R_{402}$ are as defined above, may be prepared by processes analogous to those described in Charts A, B and C above by using as starting materials the appropriate aldehyde of formula VII and lithiated heterocyclic compound of formula VIII, wherein the variables are as defined for formula XX.

Generally, peptides of the present invention may be prepared by either polymer assisted or solution phase peptide synthetic procedures analogous to those described hereinafter or to those methods known in the art. For example, the carboxylic moiety of $N^\alpha$-t-butyloxycarbonyl (Boc)-substituted amino acid derivatives having suitable side chain protecting groups, if necessary, may be condensed with the amino functionality of suitably protected amino acid, peptide or polymer-bound peptide using a conventional coupling protocol such as dicyclohexylcarbodiimide (DCC) and 1-hydroxybenzotriazole (HOBT) or diethylphosphoryl cyanide (DEPC) and triethylamine ($Et_3N$) in methylene chloride or dimethylformamide. The synthetic procedures used to incorporate the novel moieties herein are analgous to those described, for example, in U.S. Pat. Nos. 4,424,207; 4,470,971; 4,477,440; 4,477,441; 4,478,826; 4,478,827; 4,479,941; and 4,485,099, and co-pending application Ser. No. 753,198, filed Jul. 9, 1985, and copending application Ser. No. 825,250, filed Feb. 3, 1986, all of which are expressly incorporated by reference herein. See, also, published European patent applications 45,161; 45,665; 53,017; 77,028; 77,029; 81,783; 104,041; 111,266; 114,993; and 118,223.

Following coupling reaction completion, the $N^\alpha$-Boc moiety may be selectively removed with 45% trifluoroacetic acid with or without 2% anisole (v/v) in methylene chloride. Neutralization of the resultant trifluoroacetate salt may be accomplished with 10% diisopropylethylamine or sodium bicarbonate in methylene chloride. In the case of polymer-assisted peptide synthesis, this stepwise, coupling strategy may be partially or completely automated to provide the desired peptide-polymer intermediates. Anhydrous hydrofluoric acid treatment of the peptide-polymer intermediate may then be used to effect simultaneous protecting group removal and cleavage of the peptide from its polymeric support. A notable exception to this includes $N^{in}$-formyl-indolyl-substituted peptides in which the $N^{in}$-formyl-indolyl (FTrp) moiety is stable to TFA or HF but may be removed by $NH_3$ or NaOH. Because FTrp is somewhat unstable to base in synthetic procedures, possibly causing lower yields, it may be desirable in solution phase synthesis to introduce the FTrp-containing moiety late in the synthetic sequence so that it is not exposed to such conditions.

The incorporation of $N^{in}$-formyl-Trp into peptides of the present invention is easily accomplished because of the commercial availability of $N^\alpha$-Boc-$N^{in}$-formyl-Trp-OH. However, the $N^{in}$-formyl moiety may be introduced into indolyl-substituted amino acid derivatives or related compounds by reaction with HCl-formic acid as reported in the literature, see A. Previero et al, Biochim. Biophys.-Acta 147, 453 (1967); Y. C. S. Yang et al, Int. J. Peptide Protein Res. 15, 130 (1980).

The novel tripeptide of the formula III may be prepared by the procedures described above.

Generally, methods of alkylation useful in alkylating histidine for use in the present invention are found in Cheung, S. T. et al, Can. J. Chem., Vol. 55, pp. 906–910 (1977). However, it is now found that in Cheung, S. T. et al, methods it is critical that the reaction conditions for the alkylation of histidine be anhydrous. Further, it is now found also that during work-up instead of adding water directly to the reaction mixture, it is preferred that a buffered aqueous solution be added to the reaction mixture, for example, aqueous sodium or potassium hydrogen sulfate.

Variations in the above description for starting materials, reactants, reaction conditions and required protecting groups to obtain other such N-alkylated compounds are known to an ordinarily skilled chemist or are readily available in the literature.

These peptides may also be prepared by the standard solid phase techniques of Merrifield. Appropriate protecting groups, reagents, and solvents for both the solution and solid phase methods can be found in "The Peptides: Analysis, Synthesis, and Biology," Vols. 1–5, eds. E. Gross and T. Meienhofer, Academic Press, NY, 1979–1983.

The peptides of the present invention may be in either free form or in protected form at one or more of the remaining (not previously protected) peptide, carboxyl, amino, hydroxy, or other reactive groups. The protecting groups may be any of those known in the polypeptide art. Examples of nitrogen and oxygen protection groups are set forth in T. W. Greene, Protecting Groups in Organic Synthesis, Wiley, N.Y., (1981); J. F. W. McOmie, ed. Protective Groups in Organic Chemistry, Plenum Press (1973); and J. Fuhrhop and G. Benzlin, Organic Synthesis, Verlag Chemie (1983). Included among the nitrogen protective groups are t-butoxycarbonyl (Boc), benzyloxycarbonyl, acetyl, allyl, phthalyl, benzyl, benzoyl, trityl and the like.

The following peptides of the present invention are preferred: N-Acetyl-1-formyl-L-tryptophyl-1-prolyl-L-phenylalanyl-N-[1-(cyclohexylmethyl)-2-hydroxy-2-(2-pyrrolidinyl)ethyl]-L-histidinamide,[R-R*,S*)]bis(trifluoroacetate) (salt); N-Acetyl-1-formyl-L-tryptophyl- 1-prolyl-L-phenylalanyl-N-[1-(cyclohexylmethyl)-2-hydroxy-2-(2-pyrrolidinyl)ethyl]-L-histidinamide-[2S-[2R*(1R*,2S*)]]-bis(trifluoroacetate) (salt); and N-Acetyl-1-formyl-L-tryptophyl-1-prolyl-L-phenylalanyl-N-[1-(cyclohexylmethyl)-2-hydroxy-2-(2-pyrrolidinyl)ethyl]-histidinamide-[2R-[2R*(1R*,2R*)]]-bis(trifluoroacetate) (salt).

DESCRIPTION OF THE PREFERRED EMBODIMENTS

The following Preparations and Examples illustrate the present invention.

In the Preparations and Examples below and throughout this document:
Ac is acetyl;
AMP is 2-(aminomethyl)pyridinyl;
BOC is t-butoxycarbonyl;
BOM is benzyloxymethyl;
Bz is benzyl;
C is centigrade;
Celite is a filter aid;
DCC is dicyclohexylcarbodiimide;
DMF is dimethylformamide;
EtOAc is ethyl acetate;
FTrp is $N^{in}$-formyl-indolyl;
g is grams;
GEA is 2-(quanidylethyl)amino;
GMPMA is (3-(guanidylmethyl)phenyl)methylamino;
HPLC is high performance liquid chromatography;
$I_2$ is iodine;
Ile is isoleucine;
IR is infra red spectra;
LVA is Leu$\Psi$[CH(OH)CH$_2$]Val;
M or mol is mole;
MBA is 2-methylbutylamino (racemic or optically active);
MBAS is 2S-methylbutylamino;
Me is methyl;
min is minute;
ml is milliliter;
MS is mass spectroscopy;
NMHis is N$\alpha$-methyl-L-histidine;
NMR is nuclear magnetic resonance;
NOAl is (1-naphthyloxy)acetyl;
p-TSA salt is para-toluene sulfonic acid salt;
Ph is phenyl;
Phe is phenylalanine;
POA is phenoxyacetyl;
RIP means a compound having the formula H-Pro-His-Phe-His-Phe-Phe-Val-Tyr-Lys-OH.2(CH$_3$C(O)OH).XH$_2$O which is a known renin-inhibiting peptide.
Skellysolve 3 is as defined in the Merck Index, 10th edition;
t-BDMS is t-butyldimethylsilyl;
TFA is trifluoroacetic acid;
THF is tetrahydrofuran;
TLC is thin layer chromatography;
Tos is p-toluenesulfonyl;
Tr is trityl (triphenylmethyl);
2HPA is ($\pm$)-(2-hydroxypropyl)amino; and
UV is ultraviolet.

The wedge-shape line indicates a bond which extends above the plane of the paper relative to the plane of the compound thereon.

The dotted line indicates a bond which extends below the plane of the paper relative to the plane of the compound thereon.

EXPERIMENTAL SECTION

Preparation 1

[1-(Cyclohexylmethyl)-2-[1-[[(1,1-dimethylethyl)imino]methyl]-2-pyrrolidinyl]-2-hydroxethyl]-carbamic acid, 1,1-dimethylethyl ester,[2R*(1S*,2R*)]-($\pm$) (Formula A-3) and
[1-(Cyclohexylmethyl)-2-[1-[[(1,1-dimethylethyl)imino]methyl]-2-pyrrolidinyl]-2-pyrrobidinyl]-2-pyrrolidinyl-2-hydroxethyl]-carbamic acid, 1,1-dimethylethyl ester,[2R*(1R*,2R*)]-($\pm$) (Formula A-4) Refer to Chart A.

Pyrrolidine formamidine of formula A-2, prepared as described in A. I. Meyers et al., J. Amer. Chem. Soc., 106:3270–3276 (1984), (7.8 g) is added to 100 ml of tetrahydrofuran under nitrogen and subsequently cooled to $-80°$ C. (ether/carbon dioxide). Tert-butyl lithium (1.7 m in pentane) is then added dropwise over about 10 minutes. After complete addition, the reaction is warmed to $-25°$ C. for 1 hour. The reaction is cooled back to $-80°$ C. and the aldehyde of formula A-1 (6.37 g), in tetrahydrofuran (20 ml) is added dropwise over 1 hour. After complete addition, the reaction is stirred an additional 45 minutes at $-80°$ C. and then quenched by adding 10 ml of a saturated ammonium chloride solution. The $-80°$ C. bath is removed and the reaction is further diluted with 20% sodium hydroxide and extracted with ether. The combined extracts are combined, dried (magnesium sulfate) and solvent removed in vacuo to yield about 10 g of an oily semi-solid. The oily semi-solid is diluted with 25% ethyl acetate/-Skellysolve B and placed in the freezer overnight. 731 mg of the second title product, a white powder, is isolated via filtration. The remaining material is chromatographed over 350 g of silica gel eluting with 2.5% isopropyl amine/ethyl acetate. This column affords 1 g of a very nonpolar compound and the first title product; 2.84 g of a 1/1 mixture of the first and second title products and 1.0 g of a mixture of the second title product and the pyrrolidine formamidine. Chromatography of the first 1.0 g mixture using a 1:1:8 mixture of triethylamine/methanol/ethyl acetate (100 g silica gel) affords 400 mg of the first title product (Formula A-3). Chromatography of the 2.84 g mixture of the first and second title products (Formula A-3 and A-4) yields 1.42 g of the first title product (Formula A-3) and 800 mg of the second title product (Formula A-4). Chromatography of the final 1.0 g mixture affords 200 mg of the second title product (Formula A-4). Yield of the first title product (Formula A-3) is 1.82 g; yield of the second title product (Formula A-4) is 1.73 g.

Physical characteristics are as follows:
First title product:
Oil; IR, cm$^{-1}$: 3446, 3329, 2967, 2923, 2851, 1712, 1639, 1494, 1449, 1390, 1363, 1171.
$^1$H-NMR ($\delta$, CDCl$_3$): 7.55, 5.04, 3.75, 3.35, 1.95–0.85.
MS at m/e [C.I. ISOB]: 411, 410, 355, 353, 339, 328, 327, 183.
Exact Mass Found: 409.3297.
Second title product:
MP: 89°–95° C.
IR, cm$^{-1}$: 3276, 2950, 2921, 2867, 2854, 1687, 1631, 1527, 1463, 1448, 1374, 1365, 1271, 1180.
$^1$H-NMR ($\delta$, CDCl$_3$): 7.55, 5.12, 3.78–3.31, 2.15–0.75.

MS at m/e [Probe-EI]: 409, 336, 281, 184, 183, 154, 127, 97, 70, 58, 57, 41.

Anal. Found: C, 67.39; H, 11.14; N, 9.85.

Preparation 2

[1-(Cyclohexylmethyl)-2-hydroxy-2-(2-pyrrolidinyl)-ethyl]-[2R*(1R*,2S%)]-carbamic acid (Formula C-2) Refer to Chart C.

The second title product of Preparation 1 (Formula A-4) (710 mg) is added to 5 ml of 95% ethanol. To that solution is added 445 mg of hydrazine, followed by 3.12 mg of acetic acid. That mixture is then heated at 50° C. for 1.5 hours. The solvents and excess reagents are removed in vacuo to yield a white solid. Recrystallization from acetonitrile affords 359 mg of the title product.

Physical characteristics are as follows:

MP: 144°–5° C.

IR, cm$^{-1}$: 3351, 2953, 2920, 2868, 2853, 1682, 1536, 1459, 1446, 1377, 1365, 1279, 1174.

MS at m/e: 326, 308, 253, 225, 211, 200, 170, 156, 140, 126, 100, 70.

$^{13}$C-NMR (DMSO-d$_6$, PPM): 155.68, 77.46, 74.73, 59.34, 51.00, 45.88, 37.68, 34.10, 33.85, 31.82, 28.34, 28.23, 28.14, 26.20, 25.91, 25.49.

$^1$H-NMR ($\delta$, DMSO-d$_6$): 6.55, 6.18, 3.50, 3.05, 2.76, 1.90–0.65.

Anal. Found: C, 65.92; H, 10.81; N, 8.55.

Preparation 3

[1-Cyclohexylmethyl)-2-hydroxy-2-(2-pyrrolidinyl)-ethyl]-[2R*(1S*,2S*)]-carbamic acid (Formula B-2) Refer to Chart B.

The first title product of Preparation 1 (Formula A-3) (1.40 g) is added to 5 ml of 95% ethanol. To that solution is added 870 mg of hydrazine, followed by 6.10 mg of acetic acid. That mixture is then heated at 50° C. for 1.5 hours. The solvents and excess reagents are removed in vacuo and the resulting oil diluted with saturated sodium bicarbonate, and extracted with methylene chloride. The methylene chloride is dried (magnesium sulfate) and solvent removed in vacuo to yield a white semi-solid. Crystallization from acetonitrile affords 167 mg of the title product.

Physical characteristics are as follows:

MP: 151°–3° C.

IR, cm$^{-1}$: 3287, 2955, 2916, 2852, 1688, 1463, 1452, 1381, 1378, 1364, 1354, 1345, 1178.

MS at m/e: 326, 308, 253, 225, 211, 201, 170, 155, 140, 126, 100, 70.

$^{13}$C-NMR (DMSO-d$_6$, PPM): 155.56, 77.46, 74.91, 60.00, 49.31, 45.75, 33.91, 33.53, 32.39, 28.23, 26.30, 26.15, 25.97, 25.56.

$^1$H-NMR ($\delta$, DMSO-d$_6$): 6.03, 5.60, 3.58, 2.95, 2.75, 1.9–1.5, 1.4, 1.3–0.7.

Anal. Found: C, 66.18; H, 10.61; N, 8.37.

Preparation 4

2-[3-Cyclohexyl-2-[[(1,1-dimethylethoxy)carbonyl]-amino]-1-hydroxypropyl]-1-pyrrolidine carboxylic acid, phenylmethyl ester[2R*(1R*,2S*)]-(±) (Formula B-3) Refer to Chart B.

The title product of Preparation 3 (10 mg) is added to a saturated solution of aqueous sodium bicarbonate. To that heterogeneous mixture is added 7 µl of benzyloxycarbonyl chloride. The reaction immediately becomes homogeneous and stirring is continued for 30 minutes. The reaction is extracted with methylene chloride. The methylene chloride extracts are dried (magnesium sulfate) and the solvent removed in vacuo. Chromatography (5 g of silica gel, 5–20% ethyl acetate/Skellysolve B) affords 13 mg of the title product.

Physical characteristics are as follows:

IR, cm$^{-1}$: 3345, 3351, 2975, 2923, 2851, 1710, 1675, 1498, 1449, 1419, 1391, 1364, 1358, 1337, 1171.

$^1$H-NMR ($\delta$, CDCl$_3$): 7.4, 5.59, 5.16, 4.88, 4.05–3.60, 3.50–3.25, 2.20–0.80.

$^{13}$C-NMR (CDCl$_3$, PPM): 158.8, 155.8, 136.2, 128.6, 128.2, 128.1, 79.0, 77.3, 67.7, 61.8, 49.2, 47.4, 41.0, 34.1, 33.6, 33.2, 28.9, 28.4, 26.6, 26.5, 26.3, 24.3.

Mass spectrum (FAB [m+1]$^+$): Exact Mass Found: 461.3008.

Preparation 5

2-[3-Cyclohexyl-2-[[(1,1-dimethylethoxy)carbonyl]-amino]-1-hydroxypropyl]-1-pyrrolidine carboxylic acid, phenylmethyl ester[2R*(1R*,2R*)]-(±) (Formula C-3) Refer to Chart C.

The title product of Preparation 2 (29 mg) is added to 2 ml of 5% sodium bicarbonate. To that heterogeneous mixture is added 15.2 mg of benzyloxycarbonyl chloride. The solid that fills the flask slowly becomes a viscous oil. After stirring for 30 minutes, the reaction is diluted with methylene chloride. After several extractions with methylene chloride, the organic is dried and solvent removed in vacuo to yield a clear oil. Chromatography over silica gel (7 g) and eluting with 25% ethyl acetate/Skellysolve B affords 35 mg of the title product.

Physical characteristics are as follows:

IR, cm$^{-1}$: 3354, 2975, 2924, 2851, 1709, 1676, 1677, 1498, 1449, 1419, 1391, 1364, 1359, 1339, 1246, 1172, 1102, 697.

$^1$H-NMR ($\delta$, CDCl$_3$): 7.35, 5.14, 4.99, 3.95–3.50, 3.45–3.25, 2.05–0.61.

$^{13}$C-NMR (CDCl$_3$, PPM): 158.4, 155.9, 136.2, 128.6, 128.2, 79.0, 78.6, 67.6, 60.8, 50.0, 47.2, 35.4, 34.6, 33.8, 32.5, 28.4, 26.6, 26.4, 26.2, 24.3.

Mass spectrum (FAB [m+1]$^+$): Exact Mass Found: 461.3008.

Preparation 6

2-[3-Cyclohexyl-2-amino-1-hydroxypropyl]-1-pyrrolidine carboxylic acid, phenylmethyl ester,[2R*(1R*,2S*)]-(±) (Formula B-4) Refer to Chart B.

The title product of Preparation 4 (165 mg) is diluted with 2.5 ml of a cold mixture of trifluoroacetic acid/methylene chloride (1:1) cooled to 0° C. After stirring at 0° C. for 45 minutes, the reaction is diluted with saturated sodium bicarbonate and the pH adjusted to >10 by adding solid potassium carbonate. The reaction is extracted with methylene chloride, dried (magnesium sulfate) and solvent removed in vacuo to yield 106 mg of the amino alcohol as an oil. This material is used directly in the coupling reaction without further purification.

Preparation 7

2-[3-Cyclohexyl-2-[[2-[[(1,1-dimethylethoxy)carbonyl]-amino]-1-oxo-3-[1-[(phenylmethoxy)methyl]-1H-imidazol-4-yl]propyl]amino]-1-hydroxypropyl]-1-pyrrolidine carboxylic acid, phenylmethyl ester,[2R*[1R*,2R*-(S*)]]-(±) (Formula B-5) Refer to Chart B.

A mixture of Boc-L-His($\pi$Bom)-OH (120 mg), the amine of Preparation 6, (106 mg), diethylphosphorylcyanide (57 mg), and dimethylformamide (3 ml) is cooled to 0° C. To the mixture is added triethylamine (35 μl) dropwise over several minutes. After complete addition, the reaction is stirred at room temperature for 2 hours. The reaction is then diluted with 2/1 ethyl acetate/benzene mixture and washed with saturated sodium bicarbonate, brine and finally water. The organic is dried (magnesium sulfate) and solvent removed in vacuo to yield an oil. Chromatography (50 g silica gel, 5% triethylamine/-ethyl acetate) affords 117 mg of the title product as an oil.

Physical characteristics are as follows:

Mass spectrum (FAB [m+1]+): Exact Mass Found: 718.4186.

$^{13}$C-NMR: Approximately 2/1 mixture of l1/d1 diastereomers.

Preparation 8

N-acetyl-1-formyl-L-tryptophyl-1-prolyl-L-phenylalanyl-N-[1-(cyclohexylmethyl)-2-hydroxy-2-[1-[(phenylmethoxy)carbonyl]-2-pyrrolidinyl]ethyl]-1-[(phenylmethoxy)methyl]-L-histidinamide,[2R-[2R*(1R*,2S*)]]- (Formula B-6) Refer to Chart B.

The title product of Preparation 7 (120 mg) is debocylated by treatment with 30 ml of 50% trifluoroacetic acid/methylene chloride at 0° C. twice each for 1 hour. The residue is dissolved in 40 ml of methylene chloride and neutralized with 40 ml of saturated sodium bicarbonate. The aqueous layer is washed 3 times with methylene chloride. The organic layers are combined and dried over magnesium sulfate and the solvent removed under vacuum. The residue is combined with 107 mg of Ac-TrpFor-Pro-Phe-OH and 35 μl of triethylamine and dissolved in 10 ml of anhydrous dimethylformamide. 33 μl of diethylphosphorylcyanide is added to the above mixture at 0° C. After 2 hours, HPLC shows the reaction to be complete. The dimethylformamide is removed under vacuum. The residue is dissolved in 75 ml of ethyl acetate and washed three times with 50 ml of saturated sodium bicarbonate, water, three times with 50 ml of 10% citric acid, water and dried over magnesium sulfate. The crude protected peptide, after lyophilization, gives 100 mg of the title product, which is about 66% pure by reverse-phase HPLC: Using a Synchropak ™ C$_{18}$ analytical column (250 mm-4.6 mm) and a linear gradient (17% B for 2 minutes; 17–100% B over 20 minutes) using solvent A=10% acetonitrile/water (0.2% trifluoroacetic acid) and solvent B=70% acetonitrile/water (0.2% trifluoroacetic acid) and a flow rate of 1.5 ml/min.

EXAMPLE 1

N-Acetyl-1-formyl-L-tryptophyl-1-prolyl-L-phenylalanyl-N-[1-(cyclohexylmethyl)-2-hydroxy-2-(2-pyrrolidinyl)ethyl]-L-histidinamide,[R-R*,S*)]bis(trifluoroacetate) (salt) (Formula B-7) Refer to Chart B.

The crude protected peptide of Preparation 8 (100 mg) is placed in a hydrogen fluoride vessel along with 5 ml of anisole and frozen in liquid nitrogen. Anhydrous hydrogen fluoride (10 ml) is distilled into the vessel and warmed to 0° C. The mixture is then stirred for 1 hour at 0° C. The hydrogen fluoride/anisole is removed under vacuum. The peptide is precipitated with ethyl ether, dissolved in aqueous acetic acid and lyophilized. The crude deprotected peptide gives 40 mg (60% pure by reverse-phase HPLC, k'=7.2).

Purification

The peptide is dissolved in 2 ml of dimethylformamide and eluted on a semi-preparative reverse-phase C-18 column (2.2 cm×27.0 cm) containing Separations Group Vyadac C18. Other conditions include: a linear gradient (0% B for 15 minutes; 0–35% B over 210 minutes; and 35% B for 135 minutes) using solvent A=10% acetonitrile/water (0.2% trifluoroacetic acid), and solvent B=70% acetonitrile/water (0.2% trifluoroacetic acid); a flow rate of 2.5 ml/min and collecting 5 ml fractions; and detection at 280 nm (0.5 a.u. full scale). Fractions 161–170 are collected to give 8.8 mg of the title product (93.8% purity).

Physical characteristics are as follows:

Mass spectrum (FAB [m+H]+): m/z of 864.

Preparation 9

2-[3-Cyclohexyl-2-amino-1-hydroxypropyl]-1-pyrrolidine carboxylic acid, phenylmethyl ester,[2R*(1R*,2R*)]-(±) (Formula C-4) Refer to Chart C.

The title product of Preparation 5 (220 mg) is diluted with 2.5 ml of a cold mixture of trifluoroacetic acid/-methylene chloride cooled to 0° C. After stirring at 0° C. for 45 minutes, the reaction is diluted with saturated sodium bicarbonate and the pH adjusted to >10 by adding solid potassium carbonate. The reaction is extracted with methylene chloride, dried (magnesium sulfate) and solvent removed in vacuo to yield 144 mg of the title product as an oil. This material is used without further purification in the coupling reaction.

Preparation 10

2-[3-Cyclohexyl-2-[[2-[[(1,1-dimethylethoxy)carbonyl]amino]-1-oxo-3-]1-[(phenylmethoxy)methyl]-1H-imidazol-4-yl]propyl]amino]-1-hydroxypropyl]-1-pyrrolidine carboxylic acid, phenylmethyl ester,[2R*-[1R*,2R*(R*)]]-(±) (Formula C-5) Refer to Chart C.

A mixture of Boc-L-His($\pi$Bom)-OH (120 mg), the amine of Preparation 9 (107 mg), diethylphosphorylcyanide (57 mg), and dimethylformamide (3 ml) is cooled to 0° C. To that mixture is added triethylamine (35 μl) dropwise over several minutes. After complete addition, the reaction is stirred at room temperature for 2 hours. The reaction is then diluted with a 2/1 mixture of ethyl acetate/benzene and washed with saturated sodium bicarbonate, brine and finally water. The organic is dried (magnesium sulfate) and solvent removed in vacuo to yield an oil. Chromatography (50 g silica gel; 5% triethylamine/ethyl acetate) affords 76 mg of the title product.

Physical characteristics are as follows:

Mass spectrum (FAB [m+1]+): Exact Mass Found: 718.4186.

Preparation 11

N-Acetyl-1-formyl-L-tryptophyl-1-prolyl-L-phenylalanyl-N-[1-(cyclohexylmethyl)-2-hydroxy-2-[1-[-(phenylmethoxy)carbonyl]-2-pyrrolidinyl]ethyl]-1-[(phenylmethoxy)methyl]-L-histidinamide[2R-[2R*(1R*,2R*)]]- (Formula C-6) Refer to Chart C.

The title product of Preparation 10 (150 mg) is debocylated by treatment with 30 ml of 50% trifluoroacetic acid/methylene chloride at 0° C. twice each for 1 hour. The residue is dissolved in 40 ml of methylene chloride and neutralized with 40 ml of saturated sodium bicarbonate. The aqueous layer is washed 3 times with methylene chloride. The organic layers are combined and dried over magnesium sulfate and the solvent removed under vacuum. The residue is combined with 164 mg of Ac-Trp[For]-Pro-Phe-OH and 60 μl of triethylamine are dissolved in 10 ml of anhydrous dimethylformamide. 51 μl of diethylphosphorylcyanide is added to the 0° C. stirring solution. After 2 hours, HPLC shows the reaction to be complete. The dimethylformamide is removed under vacuum. The residue is dissolved in 75 ml of ethyl acetate and washed 3 times with 50 ml of saturated sodium bicarbonate, water, 3 times with 50 ml of 10% citric acid, water and dried over magnesium sulfate. The crude protected peptide, after lyophilization, gives 180 mg of the title product (containing two peaks: 10% of peak 1 and 38% of peak 2 by reverse-phase HPLC; $k'_1 = 12.8$, $k'_2 = 13$, refer to analytical HPLC conditions described in Preparation 8).

EXAMPLE 2

N-Acetyl-1-formyl-L-tryptophyl-1-prolyl-L-phenylalanyl-N-[1-(cyclohexylmethyl)-2-hydroxy-2-(2-pyrrolidinyl)ethyl]-L-histidinamide-[2S-[2R*(1R*,2S*)]]- bis(trifluoroacetate) (salt) (Formula C-7) and
N-Acetyl-1-formyl-L-tryptophyl-1-prolyl-L-phenylalanyl-N-[1-(cyclohexylmethyl)-2-hydroxy-2-(2-pyrrolidinyl)-ethyl]-histidinamide-[2R-[2R*(1R*,2R*)]]- bis(trifluoroacetate) (salt) (Formula C-8) Refer to Chart C.

The crude protected peptide of Preparation 11 (180 mg) is placed in a hydrogen fluoride vessel along with anisole (5 ml) and frozen in liquid nitrogen. Anhydrous hydrogen fluoride (10 ml) is distilled into the vessel and warmed to 0° C. The mixture is then stirred for 1 hour at 0° C. The hydrogen fluoride/anisole is removed under vacuum. The peptide is precipitated with ethyl ether, dissolved in aqueous acetic acid and lyophilized. The crude deprotected peptide gives 100 mg of the two title products (12% of peak one and 33% of peak two by reverse-phase HPLC; $k'_1 = 7.2$, $k'_2 = 7.6$).

Purification

The peptide is dissolved in 2 ml of dimethylformamide and eluted on a semi-preparative reverse phase C-18 column [Separations Group Vyadec C18, 2.2 cm×27.0 cm Michel-Miller glass column]. Using the following linear gradient: 0% B for 15 minutes; 0–35% B over 210 minutes; and 35% B for 105 minutes [A=10% acetonitrile/water (0.2% trifluoroacetic acid), B=70% acetonitrile/water (0.2% trifluoroacetic acid)] with a flow rate of 2.5 ml/min and collecting 5 ml fractions; detection at 280 nm (0.5 a.u. full scale). Fractions 133–142 are collected to give 20 mg of a mixture containing 37% of peak one and 33% of peak two. Fractions 143–150 are collected to give 20 mg of peak two (82% purity by reverse-phase HPLC).

Physical characteristics are as follows:

Mass spectrum (FAB [m+H]+): M/Z of 864 for both title products.

FORMULA CHART

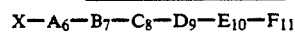    I

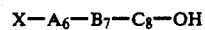    III

    V

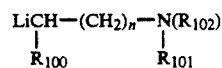    VI

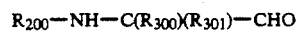    VII

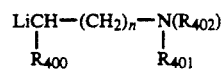    VIII

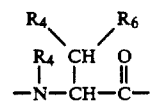    XL₂

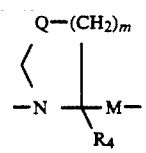    XLb

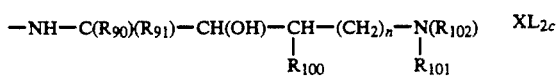    XL₂c

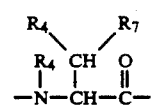    XL₃

    XX

CHART A

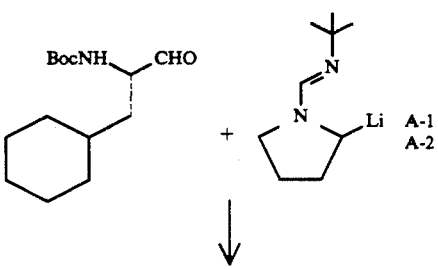

-continued
CHART A
CHART B
B-1 (A-3)
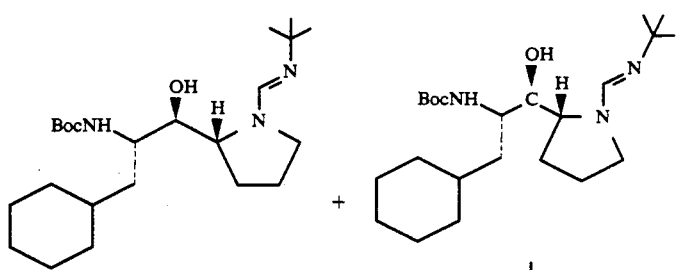
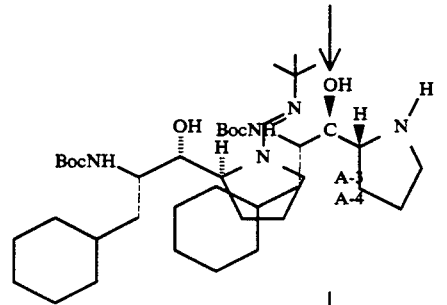
B-2
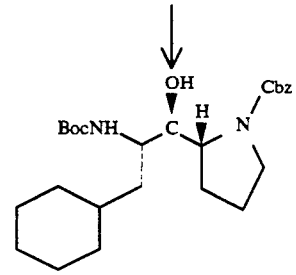
B-3
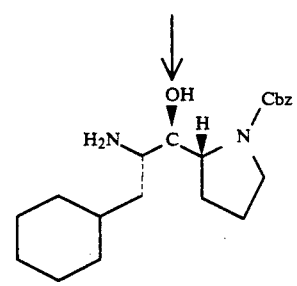
B-4

CHART B
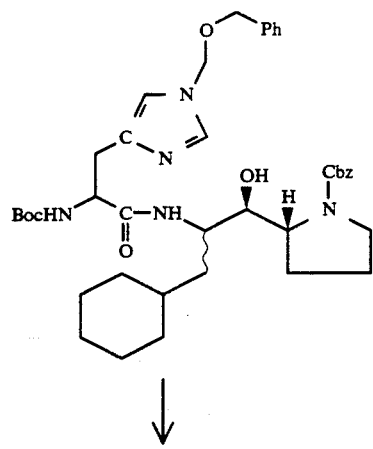
B-5
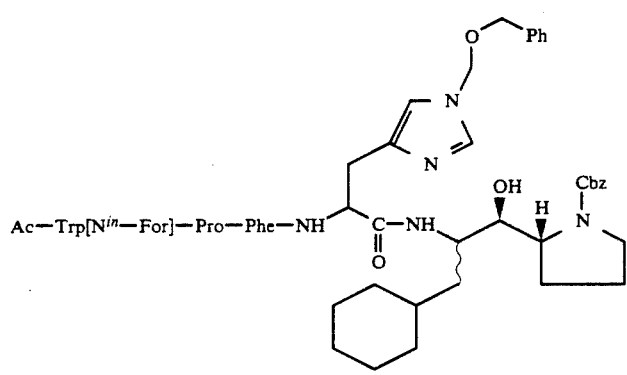
B-6
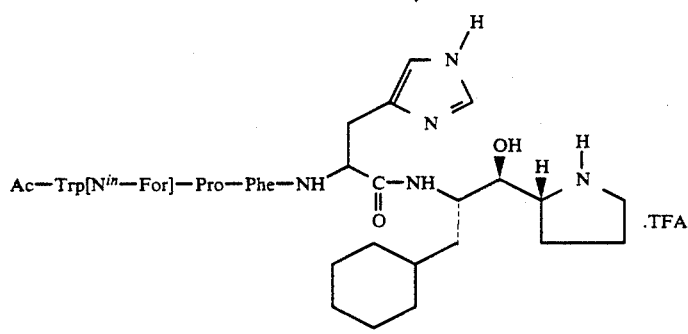
B-7
CHART C
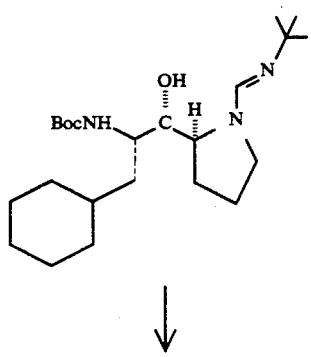
C-1 (A-4)

CHART C
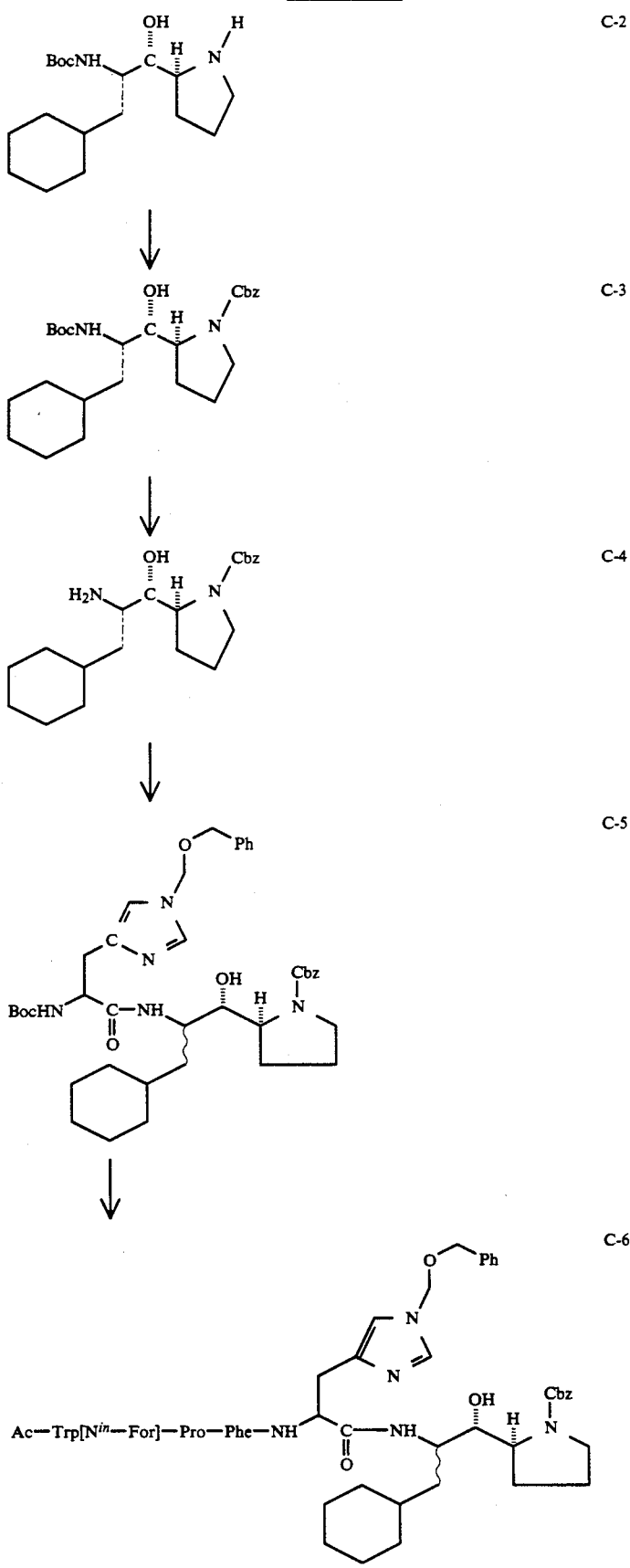

CHART C

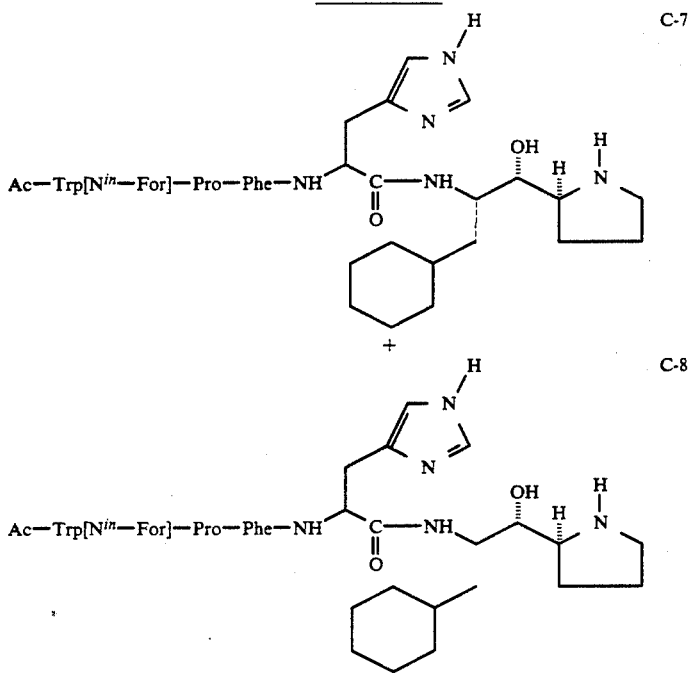

We claim:
1. A peptide of the formula I

$$X\text{-}A_6\text{-}B_7\text{-}C_8\text{-}D_9\text{-}E_{10}\text{-}F_{11} \qquad I$$

wherein X is
(a) hydrogen,
(b) $C_1\text{-}C_7$alkyl,
(c) $-(CH_2)_p$-aryl,
(d) $-(CH_2)_p$-Het,
(e) $-(CH_2)_p\text{-}C_3\text{-}C_7$cycloalkyl,
(f) $R_5-O-CH_2-C(O)-$,
(g) $R_5-CH_2-O-C(O)-$,
(h) $R_5-O-C(O)-$,
(i) $R_5-(CH_2)_n-C(O)-$,
(j) $R_5-(CH_2)_n-C(S)-$,
(k) $R_4N(R_4)-(CH_2)_n-C(O)-$,
(l) $R_5-SO_2-(CH_2)_q-C(O)-$,
(m) $R_5-SO_2-(CH_2)_q-O-C(O)-$ or
(n) $R_6-(CH_2)_i-C(O)-$;
wherein $A_6$ is a divalent moiety of the formula $XL_2$;

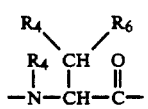

wherein $B_7$ is a divalent moiety of the formula $XL_b$;

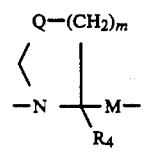

wherein $C_8$ is a divalent moiety of the formula $XL_2$;

wherein $D_9$ is a divalent moiety of the formula $XL_3$;

$$\begin{array}{c} R_4 \quad R_7 \\ R_4-CH \quad O \\ | \quad | \quad \| \\ -N-CH-C- \end{array} \qquad XL_3$$

wherein $E_{10}\text{-}F_{11}$ is a moiety of the formula $XL_{2c}$;

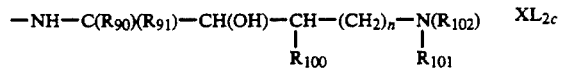

wherein $R_4$ at each occurrence is the same or different and is
(a) hydrogen,
(b) $C_1\text{-}C_7$alkyl,
(c) $-(CH_2)_p$-aryl,
(d) $-(CH_2)_p$-Het,
(e) $-(CH_2)_p-C_3-C_3-C_7$cycloalkyl, or
(f) 1- or 2-adamantyl;
wherein $R_5$ is
(a) $C_1\text{-}C_2$alkyl,
(b) $C_3\text{-}C_7$cycloalkyl,
(c) aryl,
(d) -Het, or
(e) 5-oxo-2-pyrrolidinyl;
wherein $R_6$ is
(a) hydrogen,
(b) $C_1\text{-}C_7$alkyl,
(c) $-(CH_2)_p$-aryl,
(d) $-(CH_2)_p$-Het, (e) —$(CH_2)_p$—$C_3$–$C_7$cycloalkyl, or
(f) 1- or 2-adamantyl;

wherein $R_7$ is
(a) hydrogen,
(b) $C_1$-$C_5$alkyl,
(c) hydroxy,
(d) amino $C_1$-$C_4$alkyl-,
(e) guanidinyl $C_1$-$C_3$alkyl-,
(f) aryl,
(g) -Het,
(h) methylthio,
(i) —$(CH_2)p$—$C_3$-$C_7$cycloalkyl, or
(j) amino;

wherein $R_{26}$ is
(a) hydrogen,
(b) $C_1$-$C_3$alkyl-,
(c) phenyl-$C_1$-$C_3$alkyl-;

wherein $R_{90}$ and $R_{91}$ are the same or different and are;
(a) hydrogen,
(b) $C_1$-$C_7$alkyl,
(c) —$(CH_2)_p$-aryl,
(d) —$(CH_2)_p$-Het,
(e) —$(CH_2)_p$—$C_3$—$C_3$-$C_7$cycloalkyl, or
(f) 1- or 2-adamantyl;

wherein $R_{100}$ and $R_{101}$ taken together with the carbon atom and the nitrogen atom to which they are bonded to form -Het;

wherein $R_{102}$ is
(a) hydrogen,
(b) $C_1$-$C_7$alkyl,
(c) —$(CH_2)_p$-aryl,
(d) —$(CH_2)_p$-Het,
(e) —$(CH_2)_p$—$C_3$–$C_3$-$C_7$cycloalkyl,
(f) $R_5$—O—$CH_2$—C(O)—,
(g) $R_5$—$CH_2$—O—C(O)—,
(h) $R_5$—O—C(O)—,
(i) $R_5$—$(CH_2)_n$—C(O)—,
(j) $R_5$—$(CH_2)_n$—C(S)—,
(k) $R_4N(R_4)$—$(CH_2)_n$—C(O)—,
(l) $R_5$—$SO_2$—$(CH_2)_q$—C(O)—,
(m) $R_5$—$SO_2$—$(CH_2)_q$—O—C(O)— or
(n) $R_6$—$(CH_2)_i$—C(O)—;
(o) —[C(O)—AA—NH—]$_j$X;

wherein i is zero to five, inclusive;
wherein j is one to three, inclusive;
wherein m is one or two;
wherein for each occurrence n is independently an integer of zero to five, inclusive;
wherein p is zero to two, inclusive;
wherein q is one to five, inclusive;

wherein Q is
(a) —$CH_2$—,
(b) —CH(OH)—,
(c) —O—, or
(d) —S—;

wherein M is
(a) —CO—, or
(b) —$CH_2$—;

wherein aryl is phenyl or naphthyl substituted by zero to three of the following:
(a) $C_1$-$C_3$alkyl,
(b) hydroxy,
(c) $C_1$-$C_3$alkoxy,
(d) halo,
(e) amino,
(f) mono- or di-$C_1$-$C_3$alkylamino,
(g) —CHO,
(h) —COOH,
(i) $COOR_{26}$,
(j) $CONHR_{26}$,
(k) nitro,
(l) mercapto,
(m) $C_1$-$C_3$alkylthio,
(n) $C_1$-$C_3$alkylsulfinyl,
(o) $C_1$-$C_3$alkylsulfonyl,
(p) —$N(R_4)$—$C_1$-$C_3$alkylsulfonyl,
(q) $SO_3H$,
(r) $SO_2NH_2$,
(s) —CN, or
(t) —$CH_2NH_2$;

wherein -Het is a 5- or 6-membered saturated or unstaturated ring containing from one to three heteroatoms selected from the group consisting of nitrogen, oxygen, and sulfur; and including any bicyclic group in which any of the above heterocyclic rings is fused to a benzene ring, which heterocyclic moiety is substituted with zero to three of the following:
(i) $C_1$-$C_6$alkyl,
(ii) hydroxy,
(iii) trifluoromethyl,
(iv) $C_1$-$C_4$alkoxy,
(v) halo,
(vi) aryl,
(vii) aryl $C_1$-$C_4$alkyl-,
(ix) mono- or di-($C_1$-$C_4$alkyl)amino, and
(x) $C_1$-$C_5$alkanoyl;

which nitrogen atom in the heterocyclic ring may be substituted with zero or one of the following:
(a) HC(O),
(b) t-butylcarbonyl,
(c) benzyloxycarbonyl,
(d) acetyl,
(e) allyl,
(f) phthalyl,
(g) benzyl,
(h) benzoyl, or
(i) trityl;

or a carboxy-, amino-, or other reactive group-protected form thereof;
or a pharmaceutically acceptable acid addition salt thereof.

2. The peptide of claim 1
wherein -Het is
(a) azetidinyl,
(b) pyrrolidinyl,
(c) piperidyl,
(d) 4-aryl-piperidyl,
(e) piperidino,
(f) thiazolyl,
(g) thiazenyl,
(h) piperazinyl,
(i) morpholinyl,
(j) morpholino,
(k) pyrrolinyl,
(l) 3-hydroxy-methylene-pyrrolinyl,
(m) pyrrolyl,
(n) indolyl, or
(o) 1,2,3,4-tetrahydro-isoquinolyl.

3. The peptide of claim 2
wherein X is $R_5$—O—C(O)—;
wherein $R_{90}$ is hydrogen;
wherein $R_{91}$ is methylcyclohexyl;
wherein $R_{100}$ and $R_{101}$ taken together with the carbon atom and the nitrogen atom to which they are bonded to form 2-pyrrolidinyl;

wherein $R_{102}$ is hydrogen.

4. The peptide of claim 3 selected from the group consisting of:

N-Acetyl-1-formyl-L-tryptophyl-1-prolyl-L-phenylalanyl-N-[1-(cyclohexylmethyl)-2-hydroxy-2-(2-pyrrolidinyl)ethyl]-L-histidinamide-[2S-[2R*(1R*,2S*)]]-bis(trifluoroacetate) (salt);

N-Acetyl-1-formyl-L-tryptophyl-1-prolyl-L-phenylalanyl-N-[1-(cyclohexylmethyl)-2-hydroxy-2-(2-pyrrolidinyl)ethyl]-histidinamide-[2R-[2R*(1R*,2R*)]]-bis(trifluoroacetate) (salt); and N-Acetyl-1-formyl-L-tryptophyl-1-prolyl-L-phenylalanyl-N-[1-(cyclohexylmethyl)-2-hydroxy-2-(2-pyrrolidinyl)ethyl)-L-histidinamide, [R-R*,S*)]bis(trifluoroacetate) (salt).

* * * * *